US011209358B2

(12) United States Patent
Deliwala

(10) Patent No.: US 11,209,358 B2
(45) Date of Patent: Dec. 28, 2021

(54) BLOCKING SPECULAR REFLECTIONS

(71) Applicant: Analog Devices, Inc., Norwood, MA (US)

(72) Inventor: Shrenik Deliwala, Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 0 days.

(21) Appl. No.: 16/855,279

(22) Filed: Apr. 22, 2020

(65) Prior Publication Data

US 2020/0249158 A1 Aug. 6, 2020

Related U.S. Application Data

(63) Continuation-in-part of application No. 15/457,258, filed on Mar. 13, 2017, now abandoned.
(Continued)

(51) Int. Cl.
*G01N 21/53* (2006.01)
*G08B 17/107* (2006.01)

(52) U.S. Cl.
CPC ........... *G01N 21/53* (2013.01); *G08B 17/107* (2013.01)

(58) Field of Classification Search
CPC .... G01N 21/31; G01N 21/55; G01N 21/4738; G01N 21/3554; G01N 21/314; G01N 33/18; G01N 2021/3144; G01N 21/3577; G01N 2201/0627; G01N 21/53; A61B 5/443; A61B 5/721; G01J 3/427; G08B 17/107
See application file for complete search history.

(56) References Cited

U.S. PATENT DOCUMENTS 4,398,541 A 8/1983 Pugliese
5,138,153 A 8/1992 Gergely et al.
(Continued)

FOREIGN PATENT DOCUMENTS

CN 1182572 A 5/1998
CN 101686803 3/2010
(Continued)

OTHER PUBLICATIONS

Michael L. Whiting, Measuring Surface Water in Soil with Light Reflectance, Center for Spatial Technologies and Remote Sensing, Department of Lane Air Water Resources, University of California, Davis, Proc. of SPIE vol. 7454, 7454OD © 2009 SPIE—CCC code: 0277-786X/09—doi: 10.1117/12.826896, 11 pages.

*Primary Examiner* — Blake C Riddick
(74) *Attorney, Agent, or Firm* — Patent Capital Group

(57) ABSTRACT

Device for improving an optical detecting smoke apparatus and implementing thereof. Apparatus and methods for detecting the presence of smoke in a small, long-lasting smoke detector are disclosed. Specifically, the present disclosure shows how to build one or more optimized blocking members in a smoke detector to augment signal to noise ratio. This is performed while keeping the reflections from the housing structure to a very low value while satisfying all the other peripheral needs of fast response to smoke and preventing ambient light. This allows very small measurements of light scattering of the smoke particles to be reliable in a device resistant to the negative effects of dust. In particular, geometrical optical elements, e.g., cap and optical defection elements, are disclosed.

20 Claims, 19 Drawing Sheets

Related U.S. Application Data

(60) Provisional application No. 62/375,935, filed on Aug. 17, 2016, provisional application No. 62/308,005, filed on Mar. 14, 2016.

(56) References Cited

U.S. PATENT DOCUMENTS

| | | | |
|---|---|---|---|
| 6,026,314 | A | 2/2000 | Amerov et al. |
| 6,078,833 | A | 6/2000 | Hueber |
| 6,281,498 | B1 | 8/2001 | Fellows |
| 7,616,126 | B2 | 11/2009 | Kadwell et al. |
| 8,391,943 | B2 | 3/2013 | Li et al. |
| 8,560,059 | B2 | 10/2013 | Hoarau et al. |
| 8,649,839 | B2 | 2/2014 | Chin et al. |
| 2003/0060692 | A1 | 3/2003 | Ruchti et al. |
| 2003/0060693 | A1 | 3/2003 | Monfre et al. |
| 2003/0098969 | A1 | 5/2003 | Katz et al. |
| 2003/0113924 | A1 | 6/2003 | Hazen et al. |
| 2004/0036024 | A1 | 2/2004 | Skelton |
| 2004/0068163 | A1 | 4/2004 | Ruchti et al. |
| 2004/0105021 | A1 | 6/2004 | Hu |
| 2004/0146615 | A1 | 7/2004 | McDonald et al. |
| 2005/0098713 | A1 | 5/2005 | Holland |
| 2006/0239547 | A1 | 10/2006 | Robinson et al. |
| 2008/0221406 | A1 | 9/2008 | Baker |
| 2008/0221416 | A1 | 9/2008 | Baker |
| 2008/0255433 | A1 | 10/2008 | Prough et al. |
| 2009/0318908 | A1 | 12/2009 | Van Pieterson et al. |
| 2010/0033228 | A1* | 2/2010 | Gershenfeld ........... G06F 7/388 327/334 |
| 2010/0051905 | A1 | 3/2010 | Iguchi et al. |
| 2010/0073666 | A1 | 3/2010 | Perkins et al. |
| 2010/0331636 | A1 | 12/2010 | Hubner et al. |
| 2011/0168895 | A1 | 7/2011 | Nagai et al. |
| 2012/0203086 | A1 | 8/2012 | Rorabaugh et al. |
| 2013/0158383 | A1 | 6/2013 | Cheng et al. |
| 2013/0310669 | A1 | 11/2013 | Nitzan |
| 2015/0192466 | A1 | 7/2015 | Kusukame et al. |
| 2016/0097716 | A1 | 4/2016 | Gulati et al. |
| 2016/0161415 | A1 | 6/2016 | Robinson et al. |
| 2017/0055860 | A1 | 3/2017 | Vermeulen et al. |
| 2017/0238819 | A1 | 8/2017 | Waller et al. |

FOREIGN PATENT DOCUMENTS

| | | |
|---|---|---|
| CN | 102933137 A | 2/2013 |
| CN | 103237497 | 8/2013 |
| JP | 2008/154687 A | 7/2008 |
| WO | 2015/176999 A1 | 11/2015 |
| WO | 2015176999 A1 | 11/2015 |

* cited by examiner

BLOCKING SPECULAR REFLECTIONS

CROSS-REFERENCE TO RELATED APPLICATIONS

This application is a continuation in part of U.S. patent application Ser. No. 15/457,258 entitled, "OPTICAL EVALUATION OF SKIN TYPE AND CONDITION" filed on Mar. 13, 2017, which is a non-provisional that claims the benefit of U.S. Provisional Patent Application Ser. No. 62/308,005 filed Mar. 14, 2016 and U.S. Provisional Patent Application Ser. No. 62/375,935 filed Aug. 17, 2016, all of which are hereby incorporated by reference in their entirety.

FIELD OF THE DISCLOSURE

The present invention relates to the field of optical measurements, in particular to systems and methods for evaluating skin type and/or condition based on light absorption.

BACKGROUND

Evaluation of type and condition of the skin of a living being is important in various applications. Furthermore, some applications require determination of whether a particular object being examined is skin. Skin is a complex organ and consists of many different tissue types and colored pigments that show characteristic responses when illuminated with light of different colors. These characteristic responses of various tissue types and color pigments to illumination by different colors may be exploited to evaluate properties and conditions of the skin.

For example, melanosome absorption can form basis for performing optical evaluation of skin type and condition, where spectroscopic measurements could be used to determine melanosome concentration. Skin synthesizes melanosomes. Melanosomes are specialized subunits within a cell, found in animal cells, providing the sites for synthesis, storage and transport of melanin, the most common light-absorbing pigment found in the animal kingdom. Melanosomes have strong absorption peaks in certain parts of the electromagnetic spectrum. Therefore, measurements of e.g. an absorption spectrum, i.e. variation in absorption vs. wavelength, may be used to determine the amount of melanosomes on or in a sample, providing indications of skin type and condition.

In conventional spectroscopic measurements, melanosome content of a sample is correlated to the measured spectra using chemometric models which involve using principle component analysis, first or the second derivative spectra, etc. Spectrometer equipment used in these measurements is proven and works well. However, this equipment is also bulky and expensive.

Blood provides another example of an important constituent of the skin that gives its color. The changes in the absorption spectra of the blood, based on the state of oxygenation of hemoglobin, is the basis for pulse oximetry. Spectroscopic equipment used for pulse oximetry can also be improved on.

As the foregoing illustrates, improvements in optical measurements of skin type and/or condition would be desirable.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

Aspects of the embodiments are directed to compact and non-contact systems, methods, and devices for optical detection of target chemicals on/in samples are disclosed. Light of at least two different wavelengths, or different bands of wavelengths, interacts with a target chemical, and at least some of the light that has interacted with the target chemical is incident on at least two photodetectors.

Each of the photodetectors is configured to detect light of a different wavelength, or a different band of wavelengths, that has interacted with the target chemical. A processing logic is configured to compute a ratio between a parameter indicative of the intensity of light detected by one photodetector and a parameter indicative of the intensity of light detected by the other photodetector, and to determine the presence and/or the amount of the target chemical based on the computed ratio.

According to one aspect of the present disclosure, an apparatus for optical detection of a presence and amount of a target chemical comprises a light source configured to emit light comprising a first and second wavelength, a first optical filter configured to pass light at an optical bandwidth centered about the first wavelength, a first photodetector disposed proximally to the first optical filter configured to detect light in the optical bandwidth centered about the first wavelength that has interacted with the target chemical, a second optical filter configured to pass light at an optical bandwidth centered about the second wavelength, a second photodetector disposed proximally to the second optical filter configured to detect light in the optical bandwidth centered about the second wavelength, a circuit configured to receive a first current from the first photodetector and a second current from the second photodetector; and, processing logic in electrical communication with the circuit.

According to an aspect of the present disclosure in accordance with previous embodiment, the circuit is configured to compute a ratio based on the first current and the second current, and determine at least one of the presences and the amount of the target chemical based on the computed ratio, at least in part.

According to another aspect of the present disclosure, optical detection of a presence and amount of a target chemical apparatus (or working fluid absorption device) is configure to dispose the two or detectors at two (or more accordingly) different distances from the light source with each detector measuring light transmission after two different gas absorption path lengths.

According to another aspect of the present disclosure, optical detection of a presence and amount of a target chemical apparatus (or working fluid absorption device) further comprises collector optic before the detectors.

According to another aspect of the present disclosure, optical detection of a presence and amount of a target chemical apparatus (or working fluid absorption device), the beam splitter can be a polarizing beam splitter (PBS), a half-wave plate, a half-silvered mirror, a Fresnel prism, or any other suitable optic.

According to another aspect of the present disclosure, optical detection of a presence and amount of a target chemical apparatus (or working fluid absorption device) further comprises one or more waveguides.

According to another aspect of the present disclosure, the waveguides provide for openings for the diffusion of gas molecules.

According to another aspect of the present disclosure, the optical filter can include an absorptive filter and/or interference or dichroic filter.

According to another aspect of the present disclosure, the optical detection of a presence and amount of a target chemical apparatus (or working fluid absorption device) further comprises a fiber-Bragg grating (FBG).

According to another aspect of the present disclosure, the light source can include a light emitting device (LED) or other suitable device.

According to another aspect of the present disclosure, the collection optics can include a convex or concave lens.

According to another aspect of the present disclosure, the detectors are photosensitive elements and can be one or more of the following: photodetectors, photodiodes (PDs), avalanche photodiodes (APDs), single-photon avalanche photodiode (SPADs), photomultipliers (PMTs).

According to another aspect of the present disclosure, the differences in the path length is employed after filtering of the light source for a specific gas absorption.

According to another aspect of the optical detection of a presence and amount of a target chemical apparatus (or working fluid absorption device), a ratio of the two detector signals is used to measure the concentration of the working fluid.

According to another aspect of the optical detection of a presence and amount of a target chemical apparatus (or working fluid absorption device), the ratio of the two detectors is saved during calibration step with known condition and subsequently used for future calculations.

According to another aspect of the optical detection of a presence and amount of a target chemical apparatus (or working fluid absorption device), concentration of a predetermined gas is calculated.

According to another aspect of the present disclosure, the predetermined gas may be CO2, water vapor, methane CH4, NO, as well as vapors of various alcohols.

According to another aspect of the present disclosure, the predetermined gas may be any of the gases used in anesthesia.

According to another aspect of the present disclosure, the predetermined gas may be vapors of diesel, kerosene, or gasoline.

According to another aspect of the present disclosure, multiple gases may be simultaneously detected by using multiple detectors with optical filters chosen for each of the gases and using a broadband light source.

According to another aspect of the present disclosure, the predetermined gases may be CO2 and alcohol vapor which are simultaneously detected for breadth analysis.

According to another aspect of the present disclosure, the predetermined gases may be water and alcohol vapor which are simultaneously detected for breadth analysis.

According to another aspect of the disclosure, the optical detection of a presence and amount of a target chemical apparatus (or working fluid absorption device) is disposed on a substrate.

According to another aspect of the present disclosure, the optical detection of a presence and amount of a target chemical apparatus (or working fluid absorption device) further comprises an optical cap to which is affixed to the substrate.

According to another aspect of the present disclosure, the inner shape of the cap forms a mirror in which the mirror shape is derived from the two elliptical mirror surfaces inclined substantially at 45 degrees to provide high collection of the light source to the detector.

According to another aspect of the present disclosure, the cap provides for openings for the diffusion of gas molecules.

According to another aspect of the present disclosure, the substrate and the cap provide a method of alignment to each other.

According to another aspect of the present disclosure, the opto-electronic package for measurement of absorption of light further comprises a substrate with at least two detectors disposed thereon.

According to another aspect of the present disclosure, wherein the first detector acts as a reference detector that is measures light such that its signal is substantially insensitive to the absorption by a predetermined gas.

According to another aspect of the present disclosure, the second detector that may have either optical filter attached to it or provided on top of it to make it substantially sensitive to the absorption by the predetermined gas.

According to another aspect of the present disclosure, the opto-electronic package for measurement of absorption of light further comprises many detectors in which at least one detector acts as a reference detector and the other detectors optical filters have applied to them so as to detect different gases present in the cavity.

According to another aspect of the present disclosure, the light source may be a thermal light source.

According to another aspect of the present disclosure, the opto-electronic package for measurement of absorption of light further comprises a substrate with a light source disposed on it. LED may have a center wavelength from 0.2-12 μm.

According to another aspect of the present disclosure, the detector may use direct photon absorption or may use indirect method of measurement that includes conversion to heat to measure light flux.

According to another aspect of the present disclosure, direct photon detectors include detectors made from PbSe, PbS, HgCdTe, GaSb/InAs superlattice etc.

According to another aspect of the present disclosure, indirect thermal detectors include pyroelectrics, bolometers, etc.

According to another aspect of the present disclosure, a first ratio measures the incident reflection which directly reflection from a skin, tissue or surface.

According to another aspect of the present disclosure, a second ratio measures scattering and/ absorption of a target chemical in the tissue itself.

According to another aspect of the present disclosure, a third ratio is calculated based upon the first and second ratios thereby subtracting the background. That is, the reflection stemming from the first ratio.

The drawings show exemplary detection circuits and configurations. Variations of these circuits, for example, changing the positions of, adding, or removing certain elements from the circuits are not beyond the scope of the present invention. The illustrated detectors, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1:
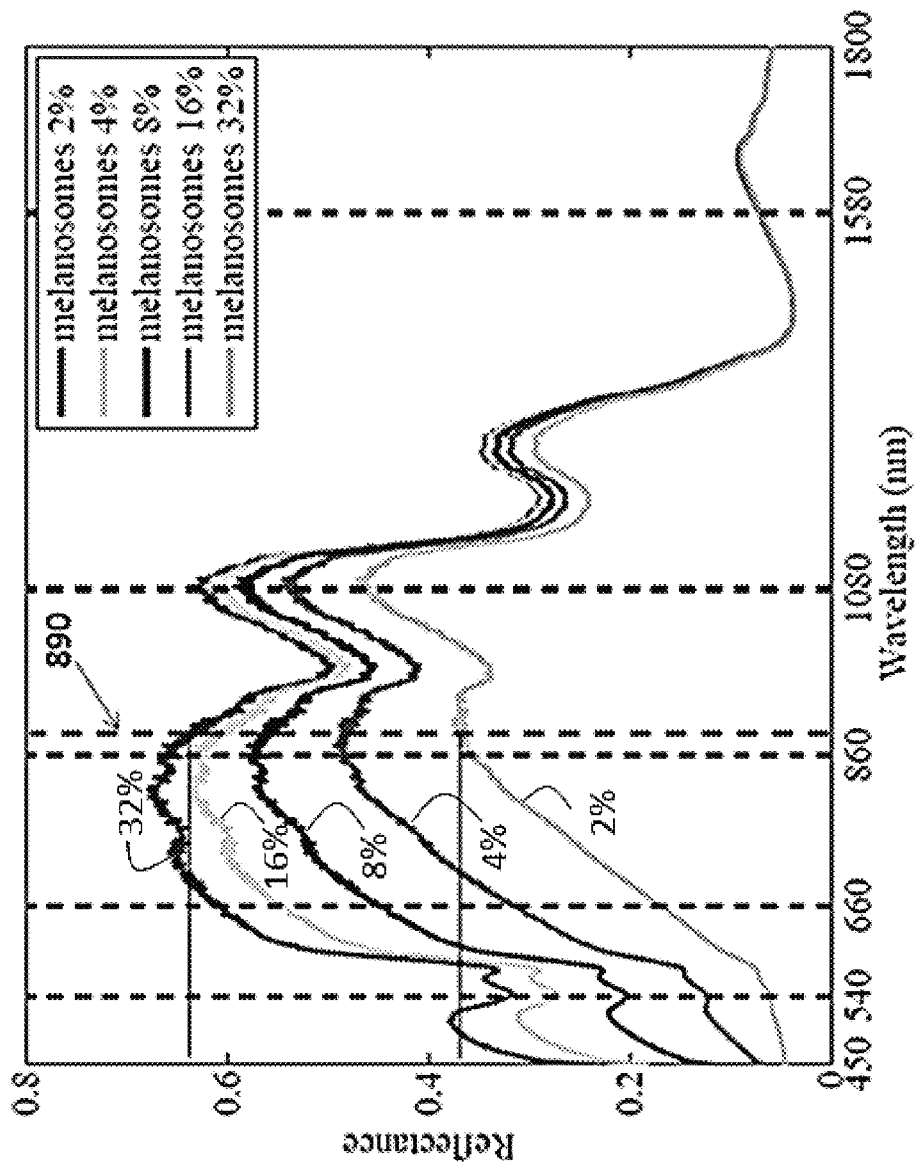
FIG. 1 illustrates spectra indicative of melanosome absorption, in accordance with some embodiments of the disclosure provided herein.

The present invention relates to the field of optical measurements, in particular to systems and methods for evaluating skin type and/or condition based on light absorption. The inventor of the present disclosure contemplates shining light into skin tissue and comparing the reflection to a reference while mitigating specular reflections.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

Embodiments of the present disclosure provide optical measurement assemblies that are compact, substantially less complex, and relatively inexpensive compared to complex spectrometer equipment that could be used to achieve comparable results. Optical measurement assemblies described herein may be used in any systems that require determination of presence and, possibly, the amount of melanosomes in a sample. Assemblies described herein may be especially attractive for, but are not limited to, cosmetic and medical applications.

In some aspects, techniques for optical detection of a presence and/or an amount of melanosomes in a sample are disclosed. The sample can be a skin sample or area of skin. Light of at least two different wavelengths, or of two different bands of wavelengths can be emitted from a single light source that is sufficiently broadband to cover both the wavelengths. The light can be directed to and interact with a region of the sample that is suspected of containing the melanosomes (the term interact can include e.g., being reflected from a sample that may comprise melanosomes, being transmitted through the sample, being partially absorbed by the sample, etc.).

At least some of the light that has interacted with the region of the sample that is suspected of containing the melanosomes is incident on at least two photodetectors (i.e. on one or more photosensitive elements of each photodetector). Each of the photodetectors is configured to detect light of a different wavelength, or a different band of wavelengths, that has interacted with the region of the sample that is suspected of containing melanosomes. A processing logic is configured to compute a ratio between a parameter indicative of the intensity of light detected by one photodetector and a parameter indicative of the intensity of light detected by the other photodetector.

The processing logic can determine the presence and/or the amount of melanosomes based on the computed ratio. In this manner, a simple, compact, and non-contact optical measurement assembly for assessing skin type and condition using differential spectral measurements may be provided.

Techniques described herein are described with reference to melanosomes being an exemplary target chemical of interest that is characteristic of skin type and condition. However, the techniques described herein are by no means limited to detecting presence and/or an amount of melanosomes, and can be extended to measurements of other target chemicals that may be characteristic of skin type and condition, such as e.g. fats, proteins, etc.

Furthermore, techniques are described herein with reference to measuring melanosome content, e.g. melanosome concentration, where measuring content may include merely detecting presence or absence of melanosomes or may include assessment/evaluation of the amount of melanosomes present.

Still further, a description of melanosomes being present in or on a sample is to be understood that technique described herein may be applicable to measuring content of melanosomes only on the surface of a skin sample (i.e. "on a sample"), or within the outer-most layers of the skin sample, as well as to measuring content of melanosomes within the skin sample (i.e. "in a sample"). A person of ordinary skill in the art would immediately recognize considerations applicable to and modifications that may need to be done to the techniques described herein depending on whether melanosome content is measured in a skin sample or on a skin sample, all of which considerations and modifications being, therefore, within the scope of the present disclosure.

As will be appreciated by one skilled in the art, aspects of the present disclosure may be embodied in various manners—e.g., as a method, a system, a computer program product, or a computer-readable storage medium. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system."

Functions described in this disclosure may be implemented as an algorithm executed by one or more processing units, e.g. one or more microprocessors, of one or more computers. In various embodiments, different steps and portions of the steps of each of the examples described herein may be performed by different processing units. Furthermore, aspects of the present disclosure may take the form of a computer program product embodied in one or more computer readable medium(s), preferably non-transitory, having computer readable program code embodied, e.g., stored, thereon.

In various embodiments, such a computer program may, for example, be downloaded (updated) to the existing devices and systems (e.g. existing optical measurement modules and/or their controllers) or be stored upon manufacturing of these devices and systems.

Other features and advantages of the disclosure are apparent from the following description, and from the selected examples.

Basics of Optical Spectrometers

Spectrometers are devices that analyze intensities and other characteristics of received signals as a function of wavelength, frequency, energy, momentum, or mass in order to characterize matter (referred to in the following as "target chemical"). Optical spectrometers are spectrometers that analyze optical spectrum, i.e. distribution of frequencies or wavelengths, of electromagnetic radiation received at their optical input.

Optical spectrometers are typically used to detect and quantify presence of various atoms and molecules in a certain region, substance, or material that the radiation passed through prior to being detected at the spectrometer. To that end, spectrometers measure intensity or/and polarization state of the received radiation as a function of a wavelength or any other variable indicative of the wavelength, such as e.g. frequency or energy of the received photons. Measurements may be carried out either in relative or in absolute units.

Spectrometer equipment currently used to characterize target chemicals is bulky, complex, and expensive. Therefore, improvements with respect to that are desirable, especially for low power, compact deployment for measuring particular chemicals.

Melanosome Absorption

As previously described herein, melanosomes have characteristic strong absorption peaks in certain parts of the electromagnetic spectrum. This can be seen in FIG. 1 illustrating spectra of skin reflectance measurements for different melanosome concentrations. As can be seen in FIG. 1, the curves have relatively strong absorption (low reflectance) at a wavelength of around 540 nm, as well as relatively strong absorption at a wavelength of around 980 nm.

Proposed Assembly for Optical Measurement of target chemical content

It has become relatively easy to find commercial light sources, e.g. light emitting diodes (LEDs), with various emission spectra. Therefore, commercial light sources with emission spectra that overlap absorption peaks of melanosomes may be found.

FIG. 1 illustrates that there are strong characteristics that are typical of the human skin and vary in a known fashion. For example, in the wavelength region between 540-600 nm, there is a strong change in reflectance whose change in reflectance depends on the skin type. Embodiments of the present disclosure are based on determining a ratio of measured light intensities of light of different wavelengths, or different bands of wavelengths, that can be indicative of the presence and/or the amount of melanosomes at one or more areas of the skin, which, in turn, could be used to assess skin type and skin condition. For example, by measuring local "color ratios" of the skin, it is possible to determine state of the skin in different layers as absorption and scattering are both functions of wavelength and depend on the structure of the skin layers.

Two or more photodetectors can measure such light of different wavelengths or different bands of wavelengths, e.g. by being provided with a suitable filter that transmits light of only certain wavelengths to the photosensitive element of the photodetectors, in particular different optical filters being provided around sharp changes in reflectance.

Figure 2A:
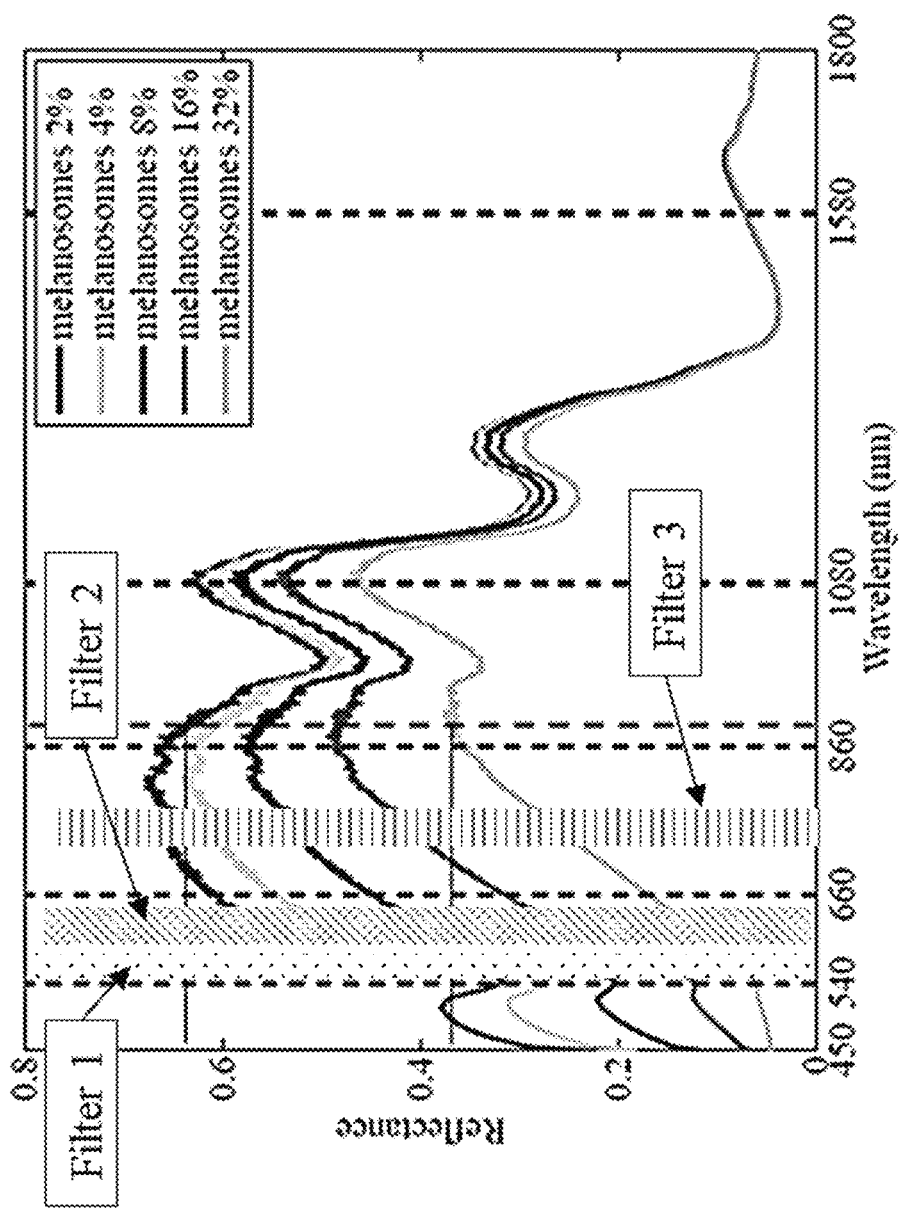
FIG. 2A illustrates spectra indicative of melanosome absorption and three exemplary idealized optical filters, according to some embodiments of the disclosure.
Figure 2B:
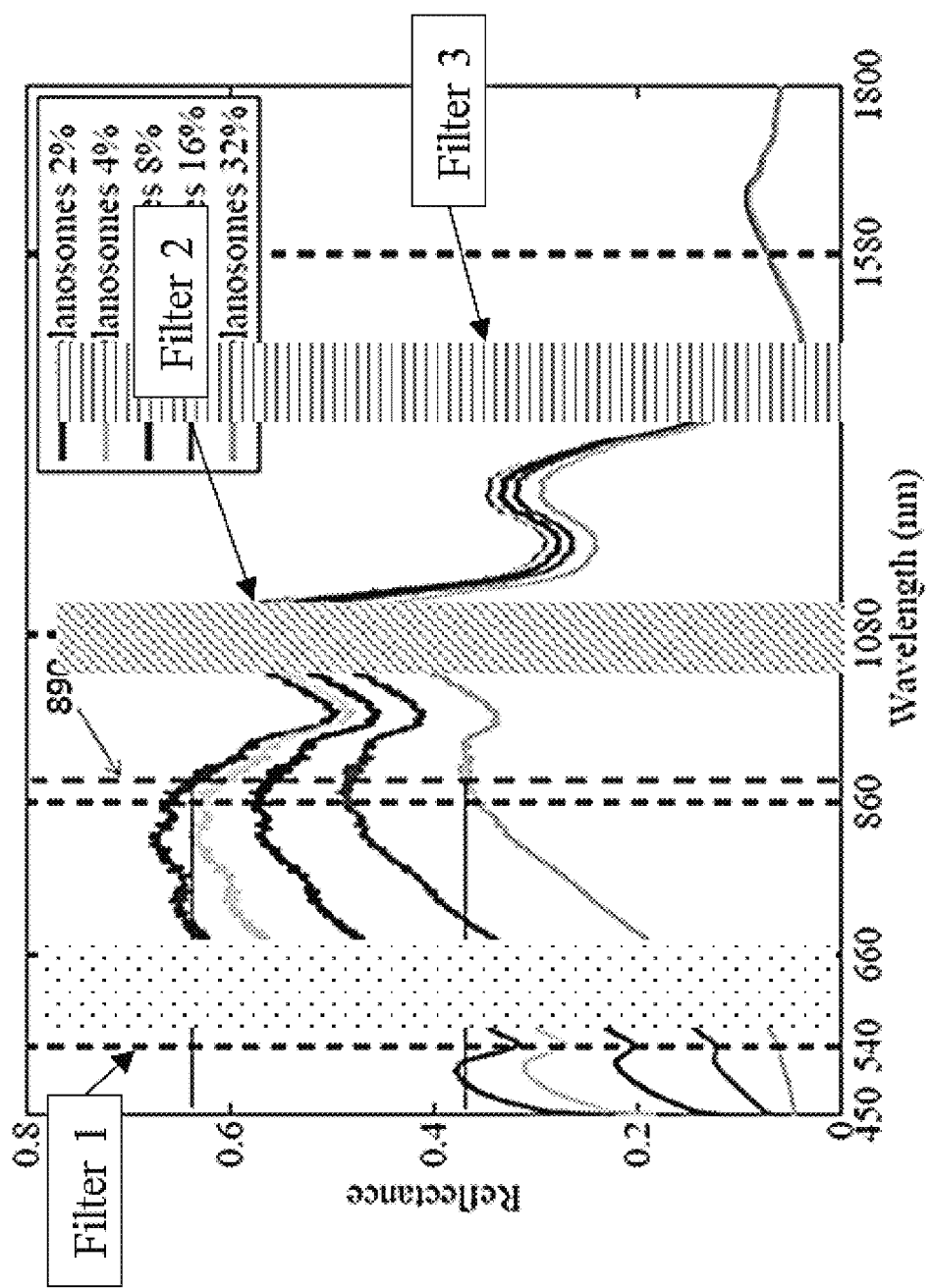
FIG. 2B illustrates spectra indicative of melanosome absorption and three exemplary idealized optical filters, according to other embodiments of the disclosure.

FIG. 2A illustrates transmission wavelength bands of three exemplary idealized filters, shown as Filter 1, Filter 2, and Filter 3, according to some embodiments of the present disclosure. FIG. 2B illustrates transmission wavelength bands of three other exemplary idealized filters Filter 1, Filter 2, and Filter 3, according to other embodiments of the present disclosure. Two or more of such filters could be used to configure respective photodetectors to detect light intensities in those bands.

Ratios as described herein may then be computed based on the outputs of at least two different photodetectors. In some embodiments, a third and further photodetectors may be additionally used to make measurements more accurate. This can also be used in conjunction with other techniques to positively identify that the reflective object is a human skin.

A typical white light LED could be used, generating light that contains all of the wavelengths of Filters 1, 2, and 3 shown in FIG. 2A. Technique discussed herein to compute ratios using normalized intensities would allow direct determination of the skin type.

In the set of filters shown in FIG. 2B, three bands at different locations are used. In this case the light source can be a broadband light source such as an incandescent light bulb. In this case, Filter 3 provides the same reflectance independent of the skin type and one can form unique ratio of Int3 to Int2 and Int1 in order to identify the skin type or the underlying skin condition. Most skin conditions change the color or the tone of the skin but currently it is difficult to determine this without the use of expensive and bulky spectrometers. For example, rapid reddening of the skin from ultraviolet damage can be measured.

Figure 3:
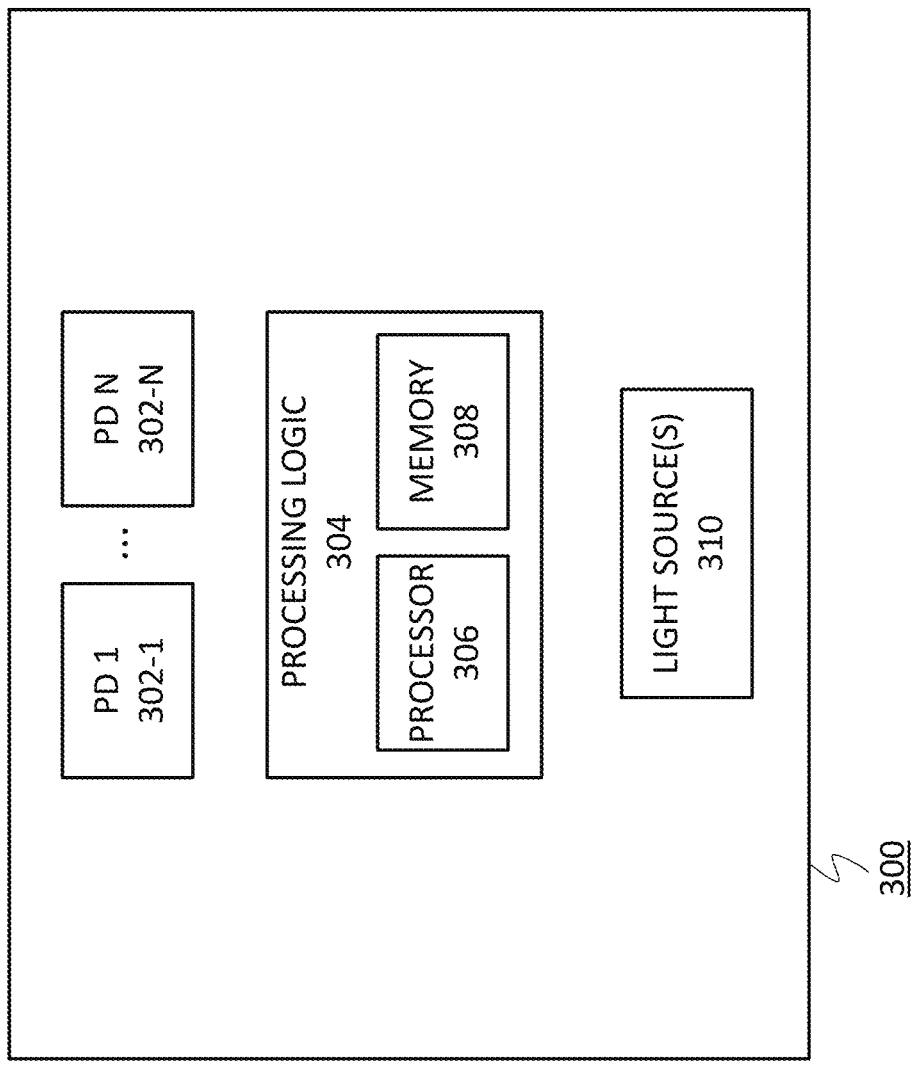
FIG. 3 illustrates an apparatus for optical detection of a presence and/or an amount of a target chemical, according to some embodiments of the disclosure.

FIG. 3 illustrates an exemplary apparatus 300 for optical detection of a presence and/or an amount of melanosomes, according to some embodiments of the disclosure. The apparatus 300 may include two or more photodetectors 302, shown in FIG. 3 as a photodetector (PD) 1 302-1, and a PD N 302-N, where N could be any integer greater than 1.

The photodetectors 302 are configured to detect light of different bands of wavelengths, where, in the context of the present disclosure, "different bands" imply that at least some of the wavelengths of one band are not included as the wavelengths of another band. Thus, two bands are considered to be different if e.g. they are partially overlapping, or if one band is included within another band (i.e. the wavelengths of one band are a subset of wavelengths of another band).

The photodetectors 302 may include any suitable photosensitive elements configured to generate an electrical signal, typically a current signal or change in resistance, in response to the light impinging onto the photoactive material of the photosensitive elements of the photodetectors. As with any detectors, the choice of a type of photodetectors used depends, first of all, on the wavelengths of radiation that each photodetector should be able to measure.

For example, in the 0.2-1.1 um spectral range (i.e. a range of radiation having wavelengths between 0.2 and 1.1 um), silicon (Si) photodetectors could be used. However, due to the energy-band structure of silicon, Si photodetectors are not suitable for detecting radiation of wavelengths beyond 1.1 um and that's where e.g. water has the strong absorption peaks that could be exploited. Instead, germanium (Ge) photodetectors could be used for detecting radiation of wavelengths beyond 1.1 um and up until about 1.7 um.

In fact, due to the energy-band structure of germanium, Ge photodetectors can be used for detecting radiation in the 0.7-1.7 um. For detecting radiation in spectral regions with wavelengths above 1.7 um, other types of detectors could be used such as e.g. InGaAs, InAs, PbS, InSb, HgCdTe, PbSe, GeAu, thermistors, bolometer, thermocouples or pyroelectric detectors.

Different photodetectors 302 could be configured to detect light of different bands by providing appropriate optical filters that filter light that reaches the photosensitive elements of the photodetectors. For example, for the example shown in FIG. 2, photodetectors each of the photodetectors PD1 and PD2 could be e.g. a Si photodetector provided with a respective band-pass optical filter so that PD1 then detects wavelengths in the band shown as e.g. Filter 1, while PD2 detects wavelengths in the band shown as Filter 2, etc. An optical filter may be provided in the form of a coating of a suitable material provided over the photosensitive region of the photodetector, as known in the art.

Each of the photodetectors 302 is configured to detect light that has interacted with a sample, if the sample is a skin sample then with the melanosomes of the skin sample, e.g. by being reflected from, transmitted through, or partially absorbed by the sample. Optionally, as shown in FIG. 3, the apparatus 300 may also include one or more light sources 310 for generating light that interacts with the sample and is then detected by the photodetectors 302. Alternatively, the one or more light sources 310 may be provided externally to the apparatus 310.

In various embodiments, the light source(s) 310 may comprise a light emitting diode (LED), an incandescent light bulb, or any suitable component(s) for emitting light. The light emitted by the light source(s) 310 can be of any suitable wavelength (or a range of wavelengths), depending on the application, as long as it includes the wavelengths or a range of wavelengths that are to be detected by the photodetectors 302 and based on which the ratios described herein are to be computed.

In order to compute the ratios, the apparatus 300 may further include a processing logic 304. The photodetectors 302 are communicatively connected to the processing logic 304 in that the results of the measurements by the photodetectors 302 can be provided to the processing logic 304.

The processing logic is configured to compute a ratio (R) between a first parameter indicative of at least an intensity of the light detected by e.g. a first photodetector PD1 (Int1) (possibly indicative of a combination of intensities of the light detected by each of the first and second photodetectors) and a second parameter indicative of at least an intensity of the light detected by a second photodetector PD2 (Int1), and determine the presence and/or the amount of melanosomes based on the computed ratio. To that end, in some embodiments, the processing logic 304 may include at least a processor 306 and a memory 308, as shown in FIG. 3, configured to implement and/or control various techniques for measuring melanosome content, described herein.

While FIG. 3 illustrates the processing logic 304 to be included within the apparatus 300, in other embodiments, the processing logic 304 may be implemented external to the apparatus 300, in which case the processing logic 304 may be configured to exchange data with the apparatus 300, in particular exchange data with the photodetectors 302 and e.g. control the light source(s) 310, remotely, via any appropriate communication channel. In other words, instead of being implemented within the apparatus 300 as shown in FIG. 3, the processing logic 304 may be external to the apparatus 300 and be communicatively coupled to the apparatus 300.

Figure 4A:
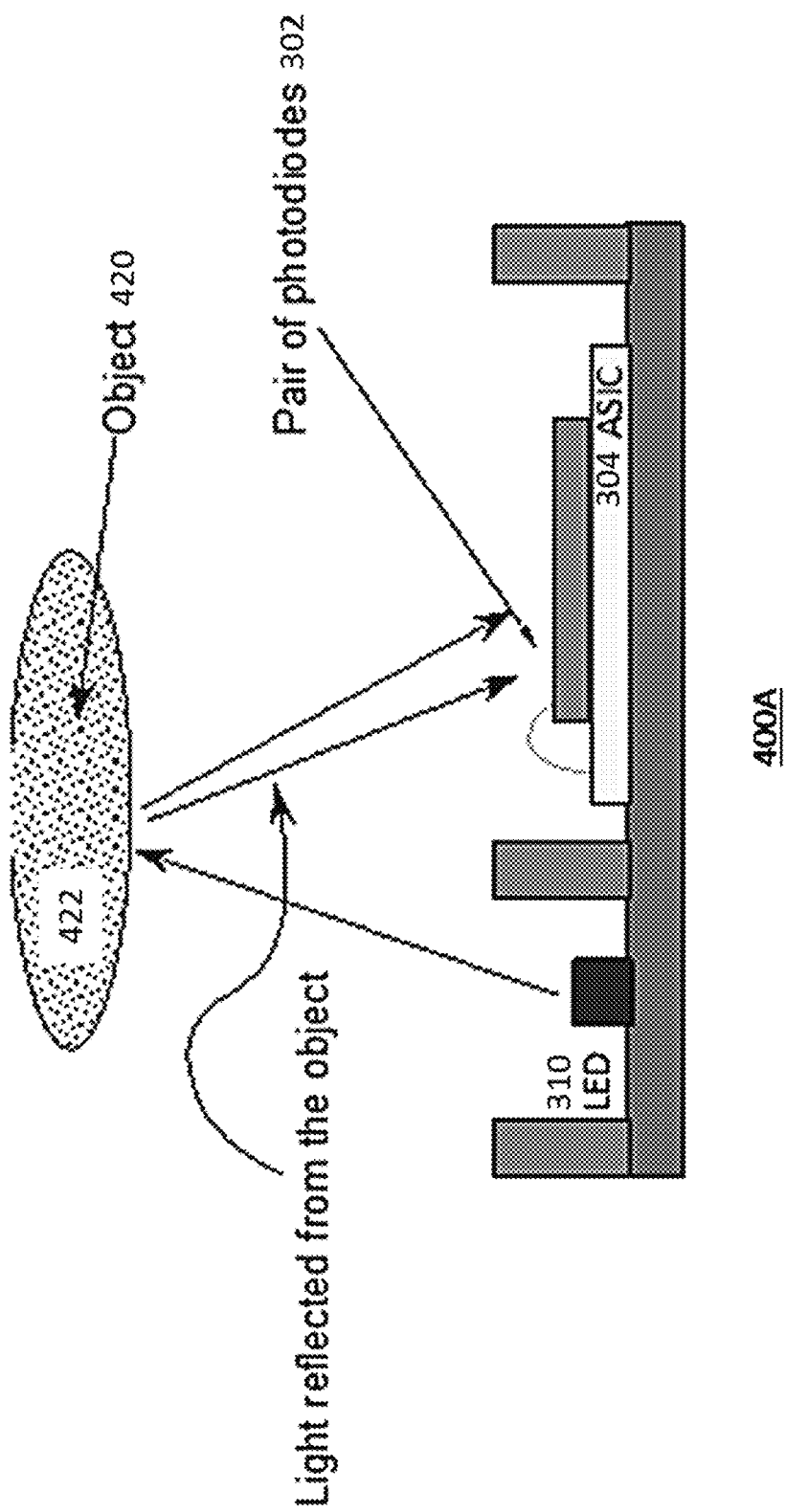
FIG. 4A illustrates relative positions of a sample and parts of an apparatus for optical detection of a presence and/or an amount of a target chemical in/on the sample for a reflection measurement, according to some embodiments of the disclosure.
Figure 4B:
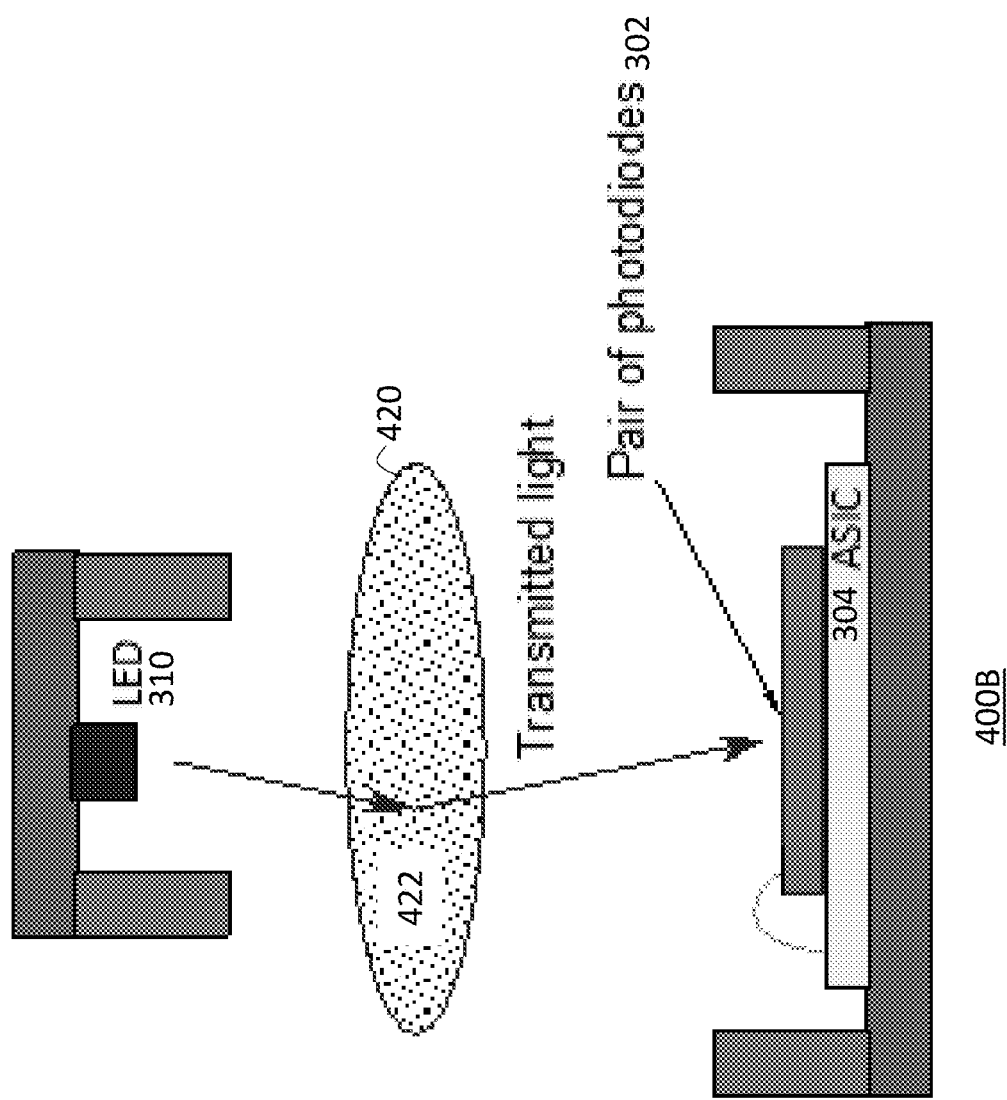
FIG. 4B illustrates relative positions of a sample and parts of an apparatus for optical detection of a presence and/or an amount of a target chemical in/on the sample for a transmission measurement, according to some embodiments of the disclosure.

Two exemplary measurement systems such as the apparatus 300 are shown in FIGS. 4A and 4B. FIGS. 4A and 4B illustrate systems 400A and 400B where the photodetectors 302 are configured to measure light that is, respectively, reflected from and transmitted through a sample 420 comprising melanosomes 422. Elements indicated in FIGS. 4A-4B by reference numerals shown in FIG. 3 are intended to represent the elements analogous to those illustrated and described with reference to FIG. 3, which description is, therefore, not repeated here.

Examples of FIGS. 4A and 4B illustrate complete measurement assemblies including the light source(s) 310, photodetectors 302, and a basic processing logic 304 shown, in these examples as an Application Specific Integrated Circuit (ASIC). In the embodiments shown in FIGS. 4A and 4B, the photodetectors 302 are shown to be mounted on top of the processing logic 304. The mounting of detectors on top of the processing logic is not necessary for the principles disclosed here but is shown here to illustrate a compact system. In other embodiments, the photodetectors 302 may be provided in any other location with respect to the processing logic 304.

In some embodiments, another feature that would contribute to providing a compact system and could, optionally, be implemented is to place the photodetectors 302 in relatively close spatial proximity to one another, e.g. less than or substantially equal to 5 mm apart. Not only would that enable a compact configuration but it would also help ensuring that the sampled reflected or transmitted light is substantially identical (i.e. that the fields of view of the photodetectors 302 overlap, at least partially), which would be advantageous because it could reduce or eliminate the issue of sampling spatially inhomogeneous scattered light from an irregular sample.

In some embodiments, another configuration that would be compact and enable the photodetectors 302 to sample substantially the same light would be to interleave photo-sensing regions of the different photodetectors. Interleaving could ensure that the measurements by different photodetectors are spatially uniform.

In some embodiments, the photodetectors 302 could be provided on the same wafer and even on the same die of a wafer. The latter would be particularly advantageous because, with the advances of semiconductor Integrated Circuit (IC) fabrication technologies, there is an ever-increasing drive to integrate devices of various functionality on a die. In general, the term "die" refers to a small block of semiconductor material on which a particular functional circuit is fabricated.

An IC chip, also referred to as simply a chip or a microchip, sometimes refers to a semiconductor wafer on which thousands or millions of such devices or dies are fabricated. Other times, an IC chip refers to a portion of a semiconductor wafer (e.g. after the wafer has been diced) containing one or more dies. In general, a system is referred to as "integrated" if it is manufactured on one or more dies of an IC chip. The system 300, or at least some portions thereof, could be provided as an integrated system.

As shown with FIGS. 4A and 4B, measurements could be performed either in reflection or in transmission. FIG. 4A illustrates that light generated by the light source 310 is reflected off of the sample 420, thereby interacting with the melanosomes 422 that may be present in the sample (melanosomes shown as dots in the sample object 420), and the reflected light is incident on the photodetectors 302. FIG. 4B illustrates that light generated by the light source 310 is transmitted through the sample 420, thereby interacting with the melanosomes 422 that may be present in the sample, and the transmitted light is incident on the photodetectors 302.

In various embodiments, ratios between parameters indicative of intensities measured by the different photodetectors 302 could be defined in different manners. Some of considerations for choosing a suitable ratio definition include e.g. a particular configuration of the system, which primarily depends on the optical filters applied to the photodetectors or bands of the wavelengths that the photodetectors are configured to measure, a particular target chemical of interest (e.g. melanosomes), and the sample material in/on which the target chemical of interest is provided. By directly comparing the output of the different optical detectors relative to one other and forming a calculated output, with a particular ratio between parameters indicative of intensities at the output of the photodetectors being one of the simplest possibilities, one can make the calculated output to be independent of the light source intensity, variations background material, gain of the system, as well as changes introduced in the light source as well as receiver electronics due to e.g. temperature. Similar performance is achieved using complex and bulky full spectroscopy systems by creating a model based on $2^{nd}$ derivative of the spectra etc.

Some exemplary ratios are now described. Based on these examples, a person of ordinary skill in the art would be able to envision implementations using other ratios and other optical filters for the photodetectors 302 to measure content of melanosomes and other target chemicals, all of which other implementations being within the scope of the present disclosure.

In one example, a spectrum of light generated by the light source(s) 310 and reflected from the object comprising a target chemical may be divided into two parts by applying appropriate optical filters to photodetectors PD1 and PD2. For example, the optical filters could be such that PD1 measures a part of the spectrum shown as Filter 1 in FIG. 2 and PD2 measures a part of the spectrum shown as Filter 2 in FIG. 2 (i.e. band-pass filters are applied). In other examples, the optical filters could be complementary to one another in that one photodetector measures all light that it can measure below a certain wavelength and another photodetector measures all light that it can measure above a certain wavelength. In such examples, by choosing appropriate filter characteristics to divide the light source spectrum into the two parts, one can directly measure the absorption by melanosomes by taking a ratio of the measured light intensities.

In various embodiments, a ratio may be computed as e.g.

$$R = \frac{Int1 - Int2}{Int1 + Int2}, R = \frac{Int1 + Int2}{Int1 - Int2}, R = \frac{Int2 - Int1}{Int2 + Int1}, R = \frac{Int2}{Int1},$$
$$R = \frac{Int1 + Int2}{Int1 - Int2}, \text{ or } R = \frac{Int1}{Int2},$$

where Int1 is a variable representative of an intensity measured by a first photodetector PD1 302-1, and Int2 is a variable representative of an intensity measured by a second photodetector PD2 302-2.

Such ratios would, advantageously, be independent of the absolute light intensity detected by the photodetectors and, hence, independent of the gain or the efficiency of the system including electronic gain, distance to the sample, sample orientation, etc., which would allow for a more accurate measurement. Presence and amount of melanosomes may then be determined based on the computed ratio.

A similar approach of using ratios as described herein may be used in determining skin hydration, i.e. amount of water present in the skin. Similar to melanosomes, water has strong absorption peaks in many parts of the electromagnetic spectrum, with some of the strongest being in the infra-red part of the spectrum (e.g. with strong absorption bands focusing around 1450 and 1930 nm wavelengths). Therefore, measurements of an absorption spectrum, i.e. variation in absorption vs. wavelength, may be used to determine the amount of water on or in a sample, e.g. skin.

Furthermore, the approach of using ratios as described herein may further be extended to evaluation of water content in applications other than those related to skin type and condition because evaluation of water content is important in applications across a large variety of fields. For example, presence of water is often detrimental to the functionality or/and the efficiency of various devices such as e.g. fuel cells, photovoltaic devices, integrated circuit (IC) chips, etc.

In another example, water content on the skin may be indicative of skin condition, such as e.g. skin dryness, and, therefore, be used in cosmetic or/and medical assessments. In yet another example, pharmaceutical industry also often needs to determine water content, e.g. in or on various chemical components. In still another example, soil moisture is also often of important and needs to be assessed.

In general, the approach of using ratios as described herein can be extended to evaluating content of many different target chemicals based on characteristic interactions of chemical with light of different wavelengths.

An example proof-of-concept procedure using water as the target chemical to be detected, and using a full spectrometer will now be described, the procedure illustrating that it is possible to determine amount of water present using ratios are described above. Theoretical and practical frameworks as to how to use ratios described herein to measure content are described thereafter. These descriptions are applicable to melanosome evaluation, pulse oximetry, and evaluations of any target chemicals having characteristic absorption bands.

Figure 5:
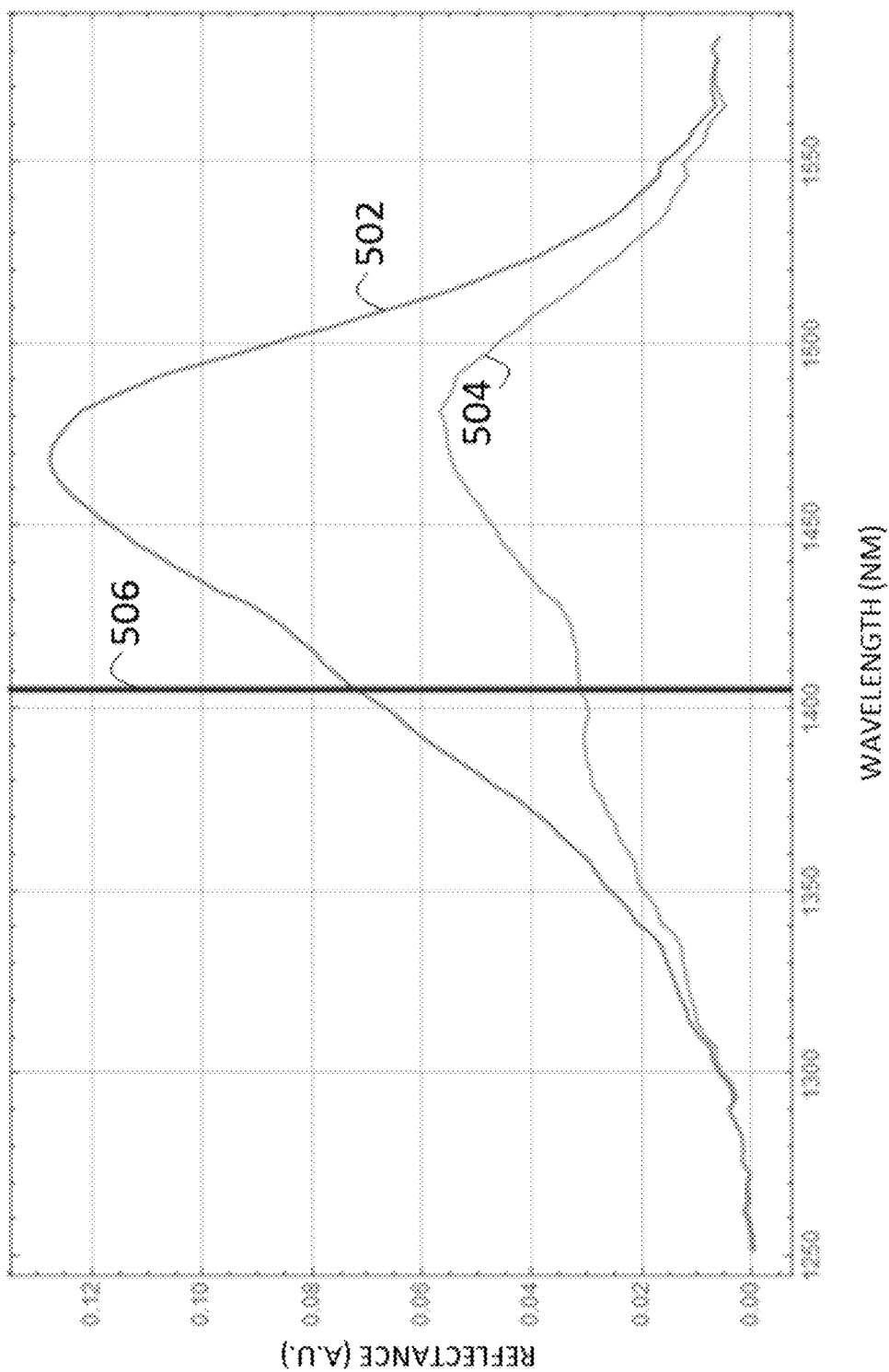
FIG. 5 illustrates an example of spectra of light reflected from samples containing different amounts of water, according to some embodiments of the disclosure.

FIG. 5 illustrates dry and wet spectra of light reflected from a sponge, as measured with a spectrometer and an LED centered around 1450 nm. In FIG. 5, line 502 illustrates spectrum for light reflected from a dry sponge and line 504 illustrates spectrum for light reflected from a wet sponge. In this case, a full spectrometer was used to illustrate the changes in the spectrum caused by the presence of water.

Line 506 in FIG. 5 indicates that, if the spectra were measured by two photodetectors where one photodetector (e.g. PD1) measured the total light for all wavelengths less than 1405 nm (Int1) and another photodetector (e.g. PD2) measured the total light for all wavelengths greater than 1405 nm (Int2), then the ratio of the output of these two detectors can be directly related to the water content of the sponge. For example, for the case shown in FIG. 5, a simple ratio $$R = \frac{Int2}{Int1},$$

as described earlier, would be 3.56 in case of a dry sponge and 2.56 in case of a wet sponge with a certain amount of water, illustrating that the ratio directly provides the ability to discriminate between wet and dry sponges. The ratio will vary smoothly for sponges containing various amounts of water and, thus, could be used to determine, at least approximately, the amount of water present.

Change in the ratio from 3.56 to 2.56 in the example described above can be explained as follows. Of the two photodetectors used, it is the photodetector PD2 that measures light at the wavelengths where water has a strong absorption peak (i.e. the absorption peak at around 1450 nm). Consider that, for a dry sponge (i.e. no, or very limited amount of water present) the ratio $$R = \frac{Int2}{Int1}$$

has a certain value. When the sponge is wet (i.e. more water present compared to the dry sponge), intensities measured by both PD1 and PD2 will be less than those measured by these photodetectors when the sponge was dry.

In addition, because absorption is stronger in the range of the PD2, due to the strong absorption peak of water in the range of PD2, intensity measured by PD2 will decrease by a factor that is greater than that of intensity measured by PD1. In other words, compared to a dry sponge, Int2 will decrease more than Int1. Therefore, the ratio for a wet sponge is less than the ratio for a dry sponge, and is indicative of the presence and the amount of water present in the sponge.

Similar reasoning applies to other target chemicals, e.g. to melanosomes, and to other ratios that may be computed when at least two photodetectors that measure different wavelength bands are used, because different wavelength bands result in different effects of absorption on the intensities measured by the photodetectors, which difference may then be used to assess presence of a target chemical.

Note in the above case, that the "dry" sponge mostly reflected the spectrum of the LED itself and hence the ratio was really the ratio of the LED spectrum as seen by the two detectors. The wet sponge simply modified this ratio as presence of water drastically changed the reflectance at different wavelengths within the spectrum of LED.

One way to relate computed ratios to the presence and/or the amounts of different target chemicals is to use theoretical models to predict what a particular ratio should be for a particular setting (i.e. given a certain light source spectrum, certain optical filters on the two or more photodetectors, a certain target chemical, and a certain sample/object in/on which the target chemical is provided).

Basic physical description of the light propagation and radiation transfer theories support the fact that the absorbance of a sample is directly proportional to the amount of target chemical, and further that the diffuse reflectance of the sample is related to the absorbance. The radiative transfer models for both reflection and transmission are well known in the literature. For example, in transmission, the Beer-Lambert law is applicable, in which $T=Exp(-A(\lambda))$, where T is the transmission and A is the total effective absorbance (including the effect of scattering) at a particular wavelength.

In reflection, more complex relationships are applicable, such as the theory of Kubelka and Monk in which the absorption coefficient is proportional to the measured reflectance $$A \propto \frac{(1-R)^2}{2R}.$$

This illustrates that there exist relationships between measured transmitted or reflected light and absorbance and, therefore, relationships between measured transmitted or reflected light and the amount of target chemical in/on a particular sample.

Theoretical models can also take into consideration further variables that affect intensities of measured transmitted or reflected light, such as e.g. scattering. Scattering coefficients are often known for the materials of interest (not only the target chemicals themselves but also the sample/objects in/on which they are provided). Scattering is wavelength dependent in that different wavelengths have different scattering coefficients.

For most materials, scattering coefficients change fairly slowly over the relatively narrow wavelength band from a light source such as an LED. For example, for the human skin, scattering coefficients have been measured and change as $\lambda^{-0.22}$, where $\lambda$ is the wavelength of radiation being scattered. Thus, there will be interplay between scattering by the material of the sample and absorption by the target chemical, e.g. water molecules or melanosomes, contained in the sample. Radiative transfer equation that includes light scattering and absorption can relate the observed reflectance or transmittance to the absorbance and scattering coefficient of the material in the sample.

In some embodiments, simplified models that relate observed reflectance or transmittance to the sample absorbance could be used, such as e.g. models based on modified Beer-Lambert's law or the Kubelka-Munk equation or many similar descriptions. In this manner, observed reflectance or transmittance can be mapped to the absorbance and further parameters such as e.g. scattering of a particular sample with a particular target chemical.

In practice, the actual spectra of the reflected or transmitted light will be fairly complex as they depend not only on the absorption by the target chemical but also on other variables, such as e.g. scattering particulate size in the material test and whether any direct light, e.g. specular reflection or directly transmitted, reaches the photodetectors. In some settings, it may be impossible or at least impractical to only use theoretically-derived relationships between the computed ratios and the amount of target chemical.

Therefore, some embodiments of the present disclosure include performing a calibration of the measurement system 300 in order to relate computed ratios to the presence and/or the amounts of different target chemicals, e.g. water or melanosomes. As used herein, calibration refers to empirically determining, in a controlled, known, environment, one or more ratios for one or more target chemicals, provided in different known amounts, in/on particular samples/objects, so that these empirical measurement can later be used to measure unknown content for the target chemicals.

In some embodiments, one or more ratios as described herein could be measured, e.g. during the manufacture of the apparatus described herein, for certain known standards, e.g. certain samples/objects with known content of certain target chemicals. Results of the calibration would be stored in, or made accessible to the measurement system 300 in any other way, providing relations between target chemicals, ratios, amounts of the target chemicals present, etc.

Subsequently, in operation (i.e. in the real, field, measurements), ratios computed based on the measured intensities as detected by the two or more photodetectors 302 are compared, e.g. by the processing logic 304, with the calibration results to assess the presence and/or amount of a certain target chemical present.

For example, the quantity of the target chemical present can be determined from the computed ratio by plotting the ratios measured for different amounts of target chemical in a controlled environment (e.g. obtained during calibration) and then using the relationship thus developed, processing logic 304 can determine the presence and/or quantity of the target chemical based on the ratio value in the plot. Of course, in other embodiments, methods other than plotting may be used for relating ratio values to quantities of the target chemicals, all of which methods being within the scope of the present disclosure.

Figure 6A:
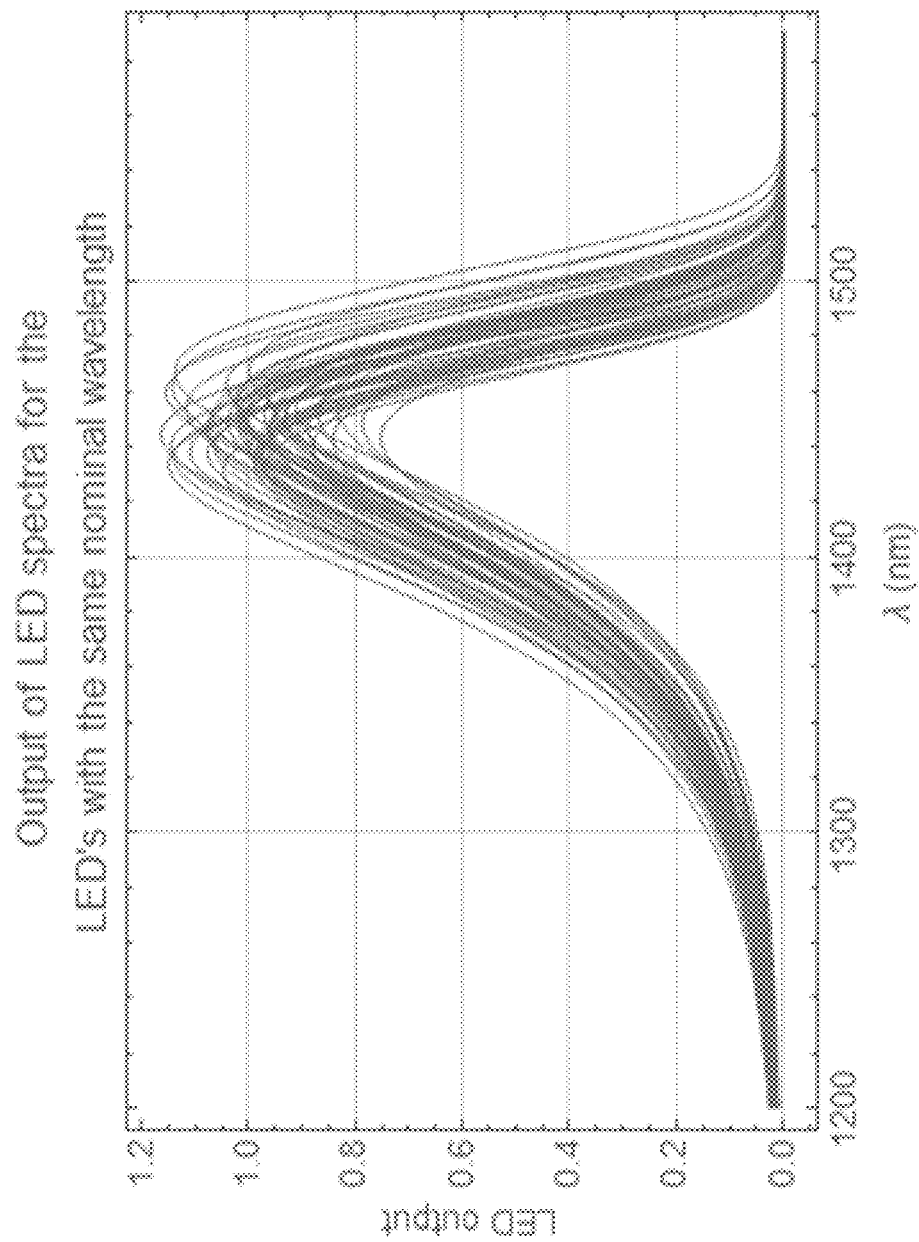
FIG. 6A illustrates variation in the exemplary LED spectra of different LEDs.

It should be noted that, in general, the shape of a spectrum of a given light source 310, e.g. an LED, will impact the measured ratio for a particular set of photodetectors 302. For example, continuing with the example of measuring water content, described with reference to FIG. 5, FIG. 6A illustrates sample spectra of commercially available 1450 nm LEDs when they are randomly chosen from a manufacturing line. As can be seen in FIG. 6A, there is a substantial variation between different LEDs.

A basic radiative transfer theory, such as e.g. the Kubelka-Munk relationship described earlier, may be used to estimate the impact of the variations in the LED spectrum on the ratios computed for a particular sample. This is illustrated in FIG. 6B, showing measured ratios for a system employing two detectors PD1 and PD2 as described above, for different amounts of water (different lines represent measurements for different LEDs of those LEDs shown in FIG. 6A).

Figure 6B:
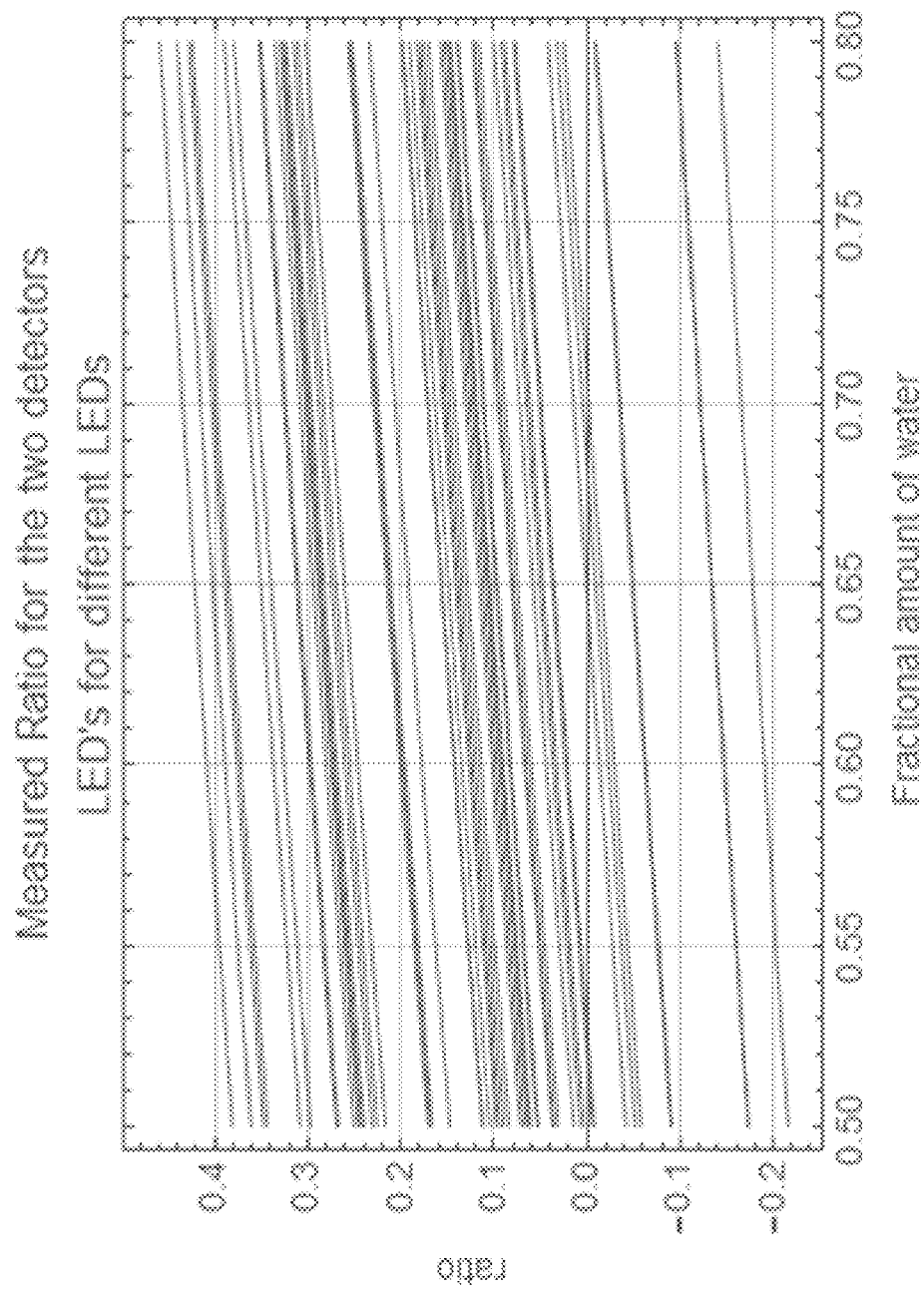
FIG. 6B illustrates measured ratios for samples containing different amounts of water when different LEDs are used.

FIG. 6B illustrates that there are substantial variations in the measured ratios, depending on which particular 1450 nm LED is used. This means that, when using such light sources, while each particular measurement system may show a good relationship, the meaning of the relationship may be compromised across the different systems using LEDs with different emission spectra.

The above-described impact to the measurement can be mitigated by normalizing the intensities measured by the different photodetectors 302 during the field measurements to the intensities measured by these photodetectors during the calibration of that particular system 300. Thus, instead of using Int1 in computing a ratio, $Int1/Int1_{cal}$ would be used, and instead of using Int2, $Int2/Int2_{cal}$ would be used.

Figure 6C:
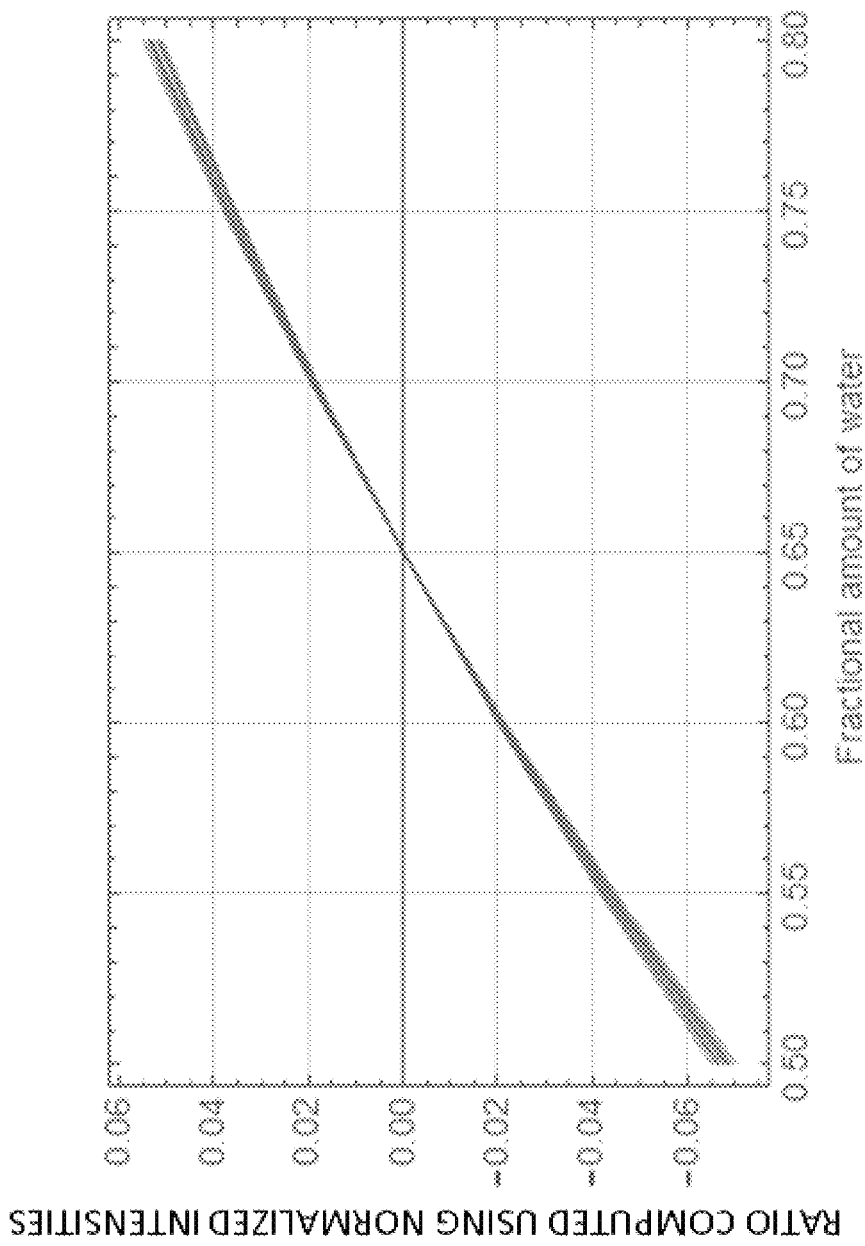
FIG. 6C illustrates ratios analogous to those shown in FIG. 6B but computed using normalized intensities, according to some embodiments of the disclosure.

Using such normalized intensities in computing a ratio makes the relationship of the computed ratio with the amount of a target chemical robust to variation in LED spectra. This is illustrated in FIG. 6C, showing ratios computed using normalized intensities for a system employing two detectors PD1 and PD2 as described above, for different amounts of water. Similar to FIG. 6B, different lines in FIG. 6C represent measurements for different LEDs of those LEDs shown in FIG. 6A. In contrast to FIG. 6B, FIG. 6C illustrates that variations in computed ratios for different LEDs are significantly reduced when normalized intensities are used for computations.

FIG. 6C illustrates ratios computed as:

$$R = \frac{\frac{Int1}{Int1_{cal}} - \frac{Int2}{Int2_{cal}}}{\frac{Int1}{Int1_{cal}} + \frac{Int2}{Int2_{cal}}}$$

In other embodiments, other ratios described herein could be re-written using normalized intensities as described above. Conversely, all of the description provided herein with respect to intensities Int1, Int2, etc., represented as absolute intensities measured by different photodetectors are applicable to normalized intensities $Int1/Int1_{cal}$, $Int2/Int2_{cal}$, etc.

Calibration is particular advantageous for the embodiments that use normalized intensities in computing the ratio because intensities are normalized based on calibration measurements in controlled environment. Such an approach allows obtaining a high quality relationship between the content of a target chemical and the measurement even when the spectrum of a light source may vary substantially from one measurement system to another.

Using normalized intensities makes the measurements robust to spectral shape variations. In some embodiments, more advanced ratios may be computed or/and optical filters may be provided onto the different photodetectors such that smooth variations in the reflectance of the sample vs. wavelength, e.g. scattering induced reflectivity changes, are also suppressed in the measurements, making the measurements even more robust.

In various embodiments of the present disclosure, optical filters on the photodetectors 302 can involve band-pass or band-stop filters, or/and at least one photodetector 302 could be provided without any additional filter. For example, a first photodetector PD1 could be provided with a band-pass filter and, thus, configured to detect light in a certain band, such as e.g. a band 706 indicated as a shaded area in FIG. 7, while a second photodetector PD2 could be left without a filter and, thus, configured to detect light in a band defined by the bandgap structure of the photosensitive material of the photodetector. This may be implemented by e.g. coating PD1 with a filter to simply pass light of specific wavelengths as shown with the range 706, while PD2 is left uncoated and thus collects light at all wavelengths that it can detect.

$$R = \frac{\alpha Int1 - \beta(Int2 - Int1)}{Int2},$$

Figure 7:
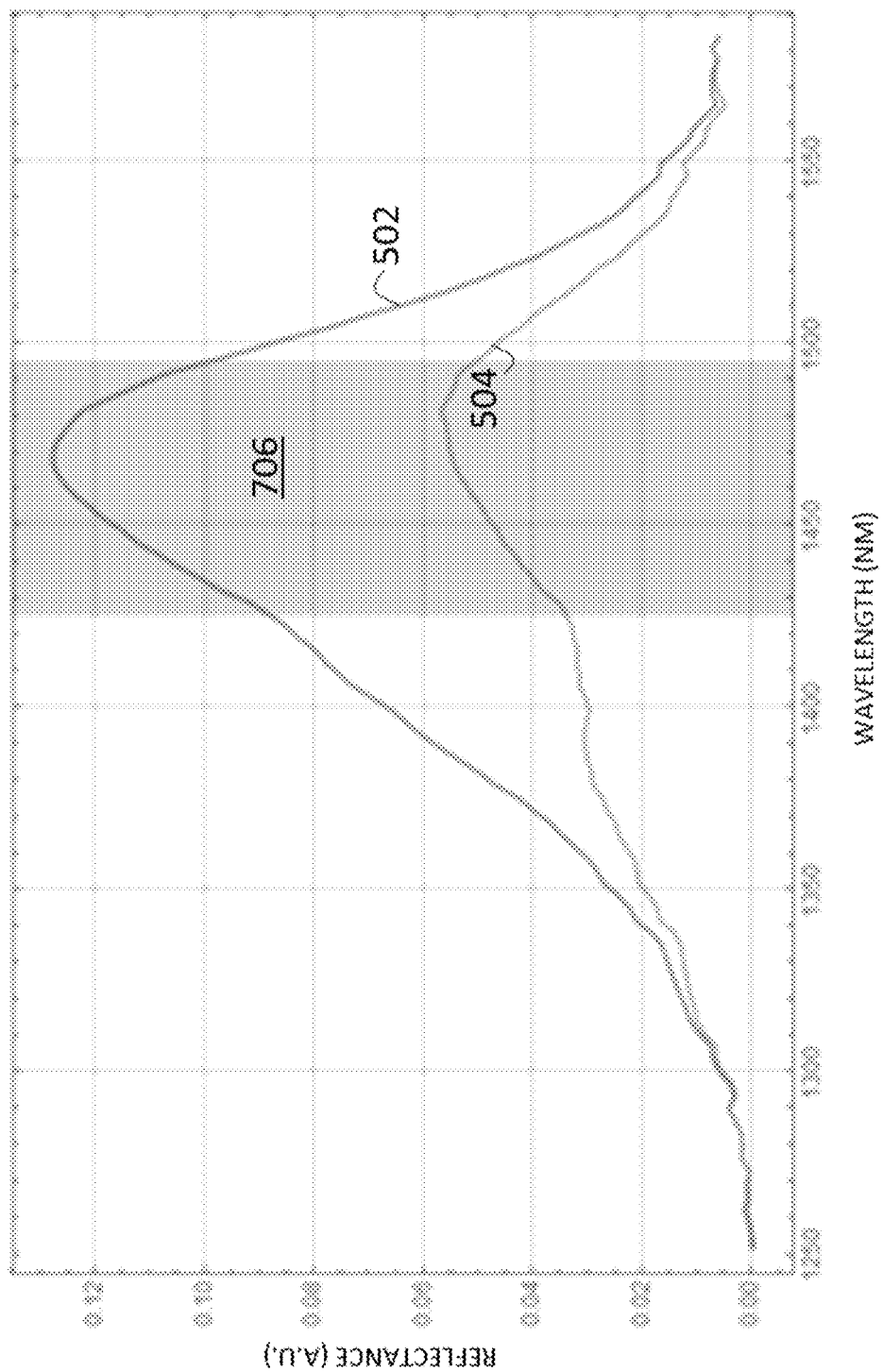
FIG. 7 illustrates an example of a spectrum of a band-pass filter provided for the example of FIG. 5, according to some embodiments of the disclosure.

In such an example, a ratio may be computed as where $\alpha$ and $\beta$ are predefined weight parameters which could be e.g. determined empirically or calculated based on one or more theoretical models. Similar to FIGS. 5 and 6A-6C, the example shown in FIG. 7 is shown for the example of measuring water content, but analogous principles apply to determining e.g. melanosome content, with the band 706 being e.g. the range of 640-890 nm or being in the range of 1000-1120 nm.

Figure 8A:
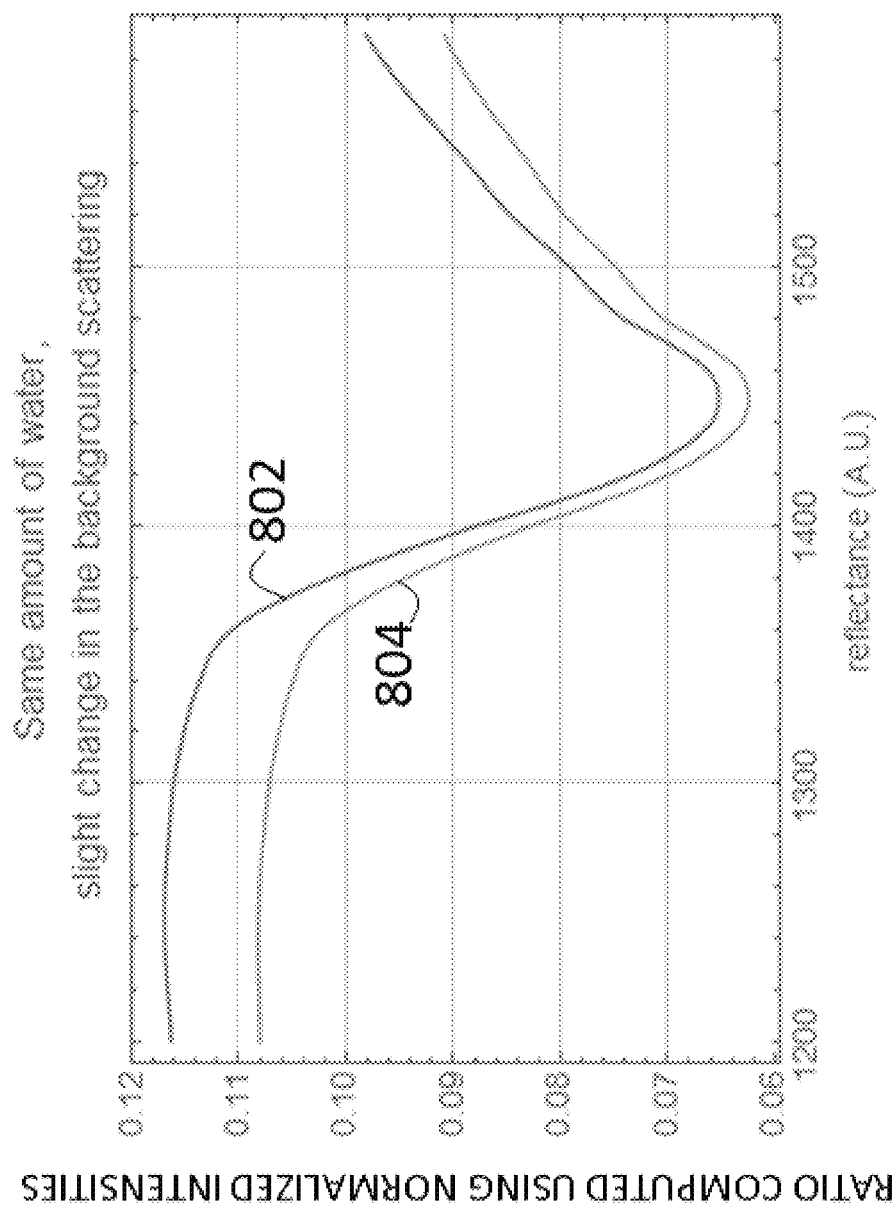
FIGS. 8A-8C illustrate how measurements can be made more robust to smooth changes in the background using weight parameters, according to some embodiments of the disclosure.
Figure 8B:
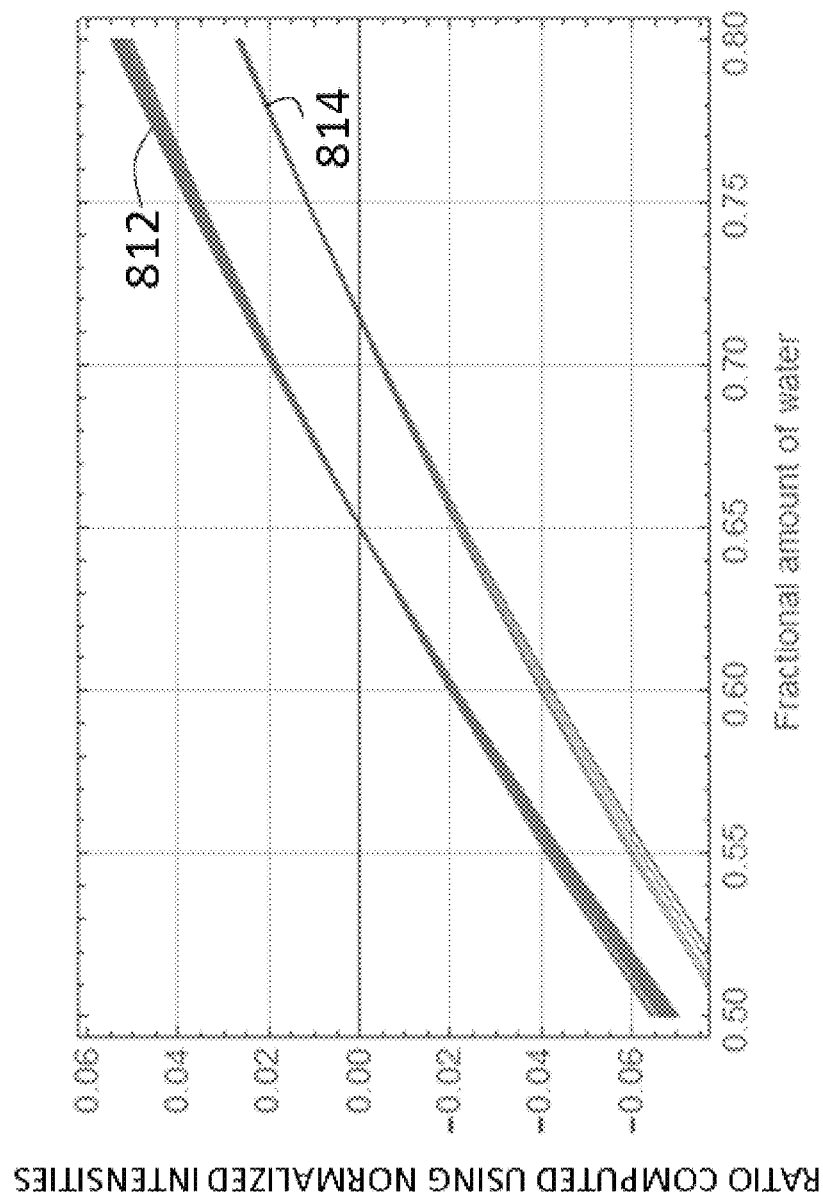
Figure 8C:
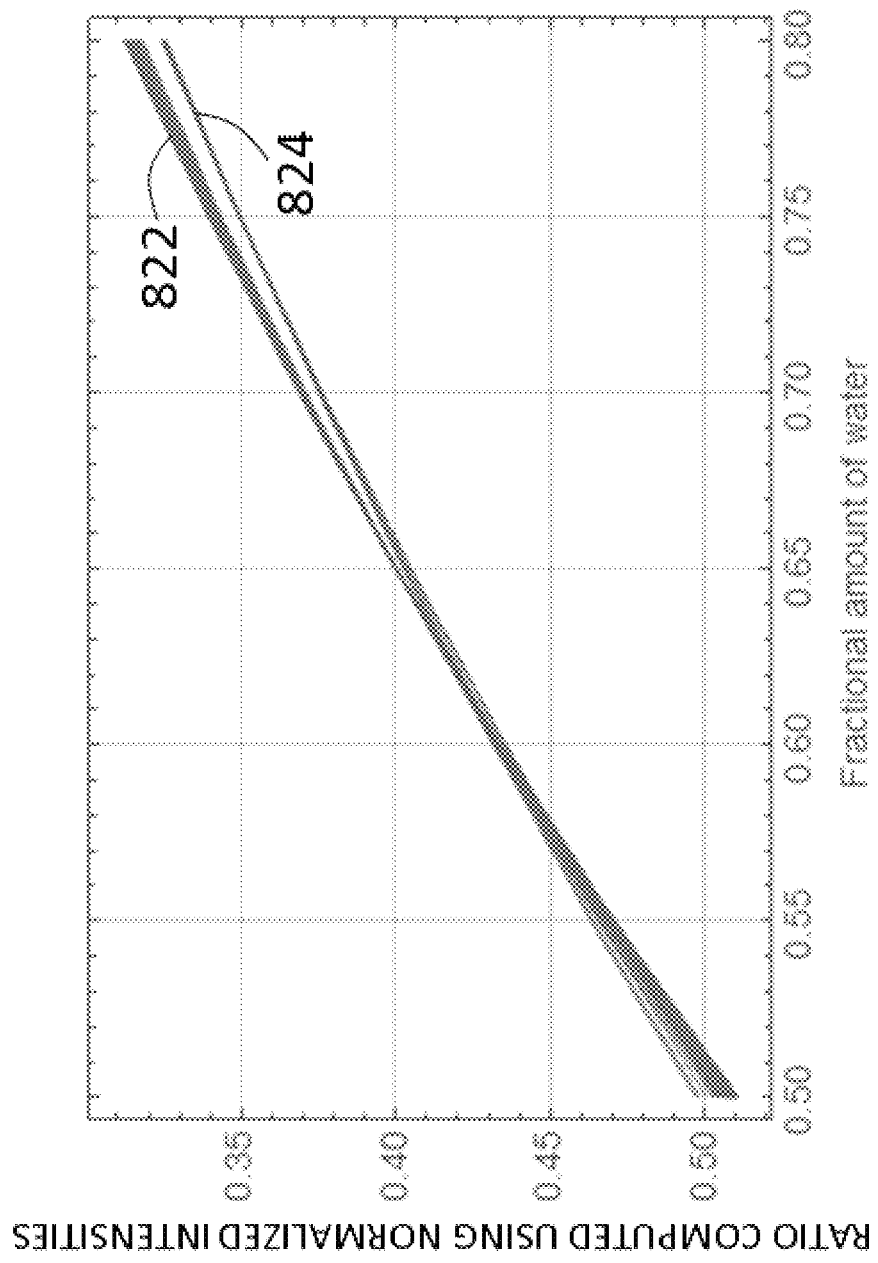

FIGS. 8A-8C illustrate how measurements can be made more robust to smooth changes in the background using weight parameters $\alpha$ and $\beta$ as described above, again provided for the example of water. For each of FIGS. 8A-8C, ratios were computed using normalized intensities (as shown with the y-axes), but in other embodiments, weight parameters can be implemented without using normalized intensities (i.e. using absolute values of the intensities). Two curves shown in FIG. 8A illustrate that, for the same amount of target chemical (water, in the example shown), there could be slight change in the background scattering.

FIG. 8B illustrates that ratios calculated without using weight parameters $\alpha$ and $\beta$ for slightly different background scattering properties of FIG. 8A. In particular, FIG. 8B illustrates a set of ratios 812 and a set of ratios 814. Both sets of ratios are computed using normalized intensities for a system employing two detectors PD1 and PD2 as described above, for different amounts of water, similar to the set of ratios shown in FIG. 6C. The set of ratios 812 corresponds to the scattering properties shown with the curve 802 in FIG. 8A, while the set of ratios 814 corresponds to the scattering properties shown with the curve 804 in FIG. 8A.

FIG. 8C illustrates sets of ratios 822 and 824, similar to sets of ratios 812 and 824, respectively, shown in FIG. 8B, except that the ratios in the illustration of FIG. 8C are computed using appropriate weight parameters $\alpha$ and $\beta$ (in the example shown, the weight parameters are equal to 1 and 1.4, respectively). FIG. 8C illustrates that variations in computed ratios for different background scattering parameters are significantly reduced when weight parameters are used.

Calculating ratios as described above may be viewed as a crude second derivative of the spectrum. As such, second derivative of a spectrum (vs. wavelength) is independent of gain, which was achieved by the first derivative and the ratios discussed in the first example, as well as any smooth variation in the absorption or reflectance across the wavelengths. Thus, the ratio becomes even more sensitive to the absorption spectrum of the target chemical.

Descriptions provided above could be generalized to embodiments where three measurements are taken, using three photodetectors configured to detect light in different bands, e.g. shown as Filter 1, Filter 2, and Filter 3 in the FIGUREs. For example, three photodetectors 302 could be used for wavelength ranges that could be referred to, relatively, as high, middle, and low wavelength regions.

Thus, in various embodiments of the present disclosure more than two photodetectors could be used and one or more ratios between parameters indicative of intensities measured by these photodetectors could be used. Such ratios could involve coefficients, similar to the coefficients $\alpha$ and $\beta$ described above, which could be chosen, e.g. determined empirically or calculated based on one or more theoretical models, to provide the best sensitivity to the target analyte.

In some embodiments, the light source(s) 310 may be modulated and the photodetectors 302 may be configured to lock onto the modulation to reduce or eliminate contamination from the ambient light at the wavelengths detected by the photodetectors. Any modulation as known in the art could be used for this purpose, such as e.g. amplitude modulation, phase modulation, polarization modulation. The other very important advantage is that the LED may be switched very rapidly and the detected signal "locked" to the LED switching to eliminate the effects of the ambient light that may also fall on the detector.

In some embodiments, two or more of the photodetectors 302 could be configured to perform their measurements substantially simultaneously, or at least during overlapping times. This could be useful for eliminating any motion induced artifacts such as e.g. when evaluating skin type or condition on a live being and part of the evaluated body, e.g. hands, being unsteady.

Descriptions provided herein for water and melanosomes can readily be extended to any other chemicals of interest that have relatively narrow absorption bands and can, therefore, be assessed using techniques of the present disclosure. For example, fats or sugars may be measured in this manner. In various embodiments, the choice of bands that different photodetectors should be configured to measure, and of the light sources to use for illuminating the target materials would depend on the particular target chemicals and target materials expected, e.g. using some of the considerations described herein.

For example, for measuring water content, an LED centered at about 1460 nm or/and an LED centered at about 1930 nm could be used as the light source(s) 310, while for measuring Erythema index, indicative of how red the skin has become after exposure to the sun, three or more colors in green, red, and IR band may be used as the light source(s) 310. In another example, for measuring fat content, an LED centered at about 1200 nm could be used. In yet another example, for measuring protein content, an LED centered at about 1300 nm could be used. Using an LED centered at about 1726 nm would allow e.g. measuring sebum, which could be relevant for cosmetic industry and skin health applications.

In other embodiments, a broadband light source may be used, e.g. a white light source, may be used. In some embodiments, an extended white light LED with phosphors that emit in the near infra-red region may be used as a light source, e.g. to measure oxygen level in the blood as a part of pulse oximetry. For more complex dermatological evaluations, light source(s) 310 may span multiple wavelengths ranging from e.g. blue to 2500 nm.

In still further embodiments, multiple systems such as the system 300 may be included or the system 300 may be provided with multiple sets of photodetectors and possibly multiple light sources emitting light in different bands, for measuring content of more than one target chemical at the same time. For example, combining light sources that measure water and melanosome contents, such a system could independently determine content of each independently.

Figure 9:
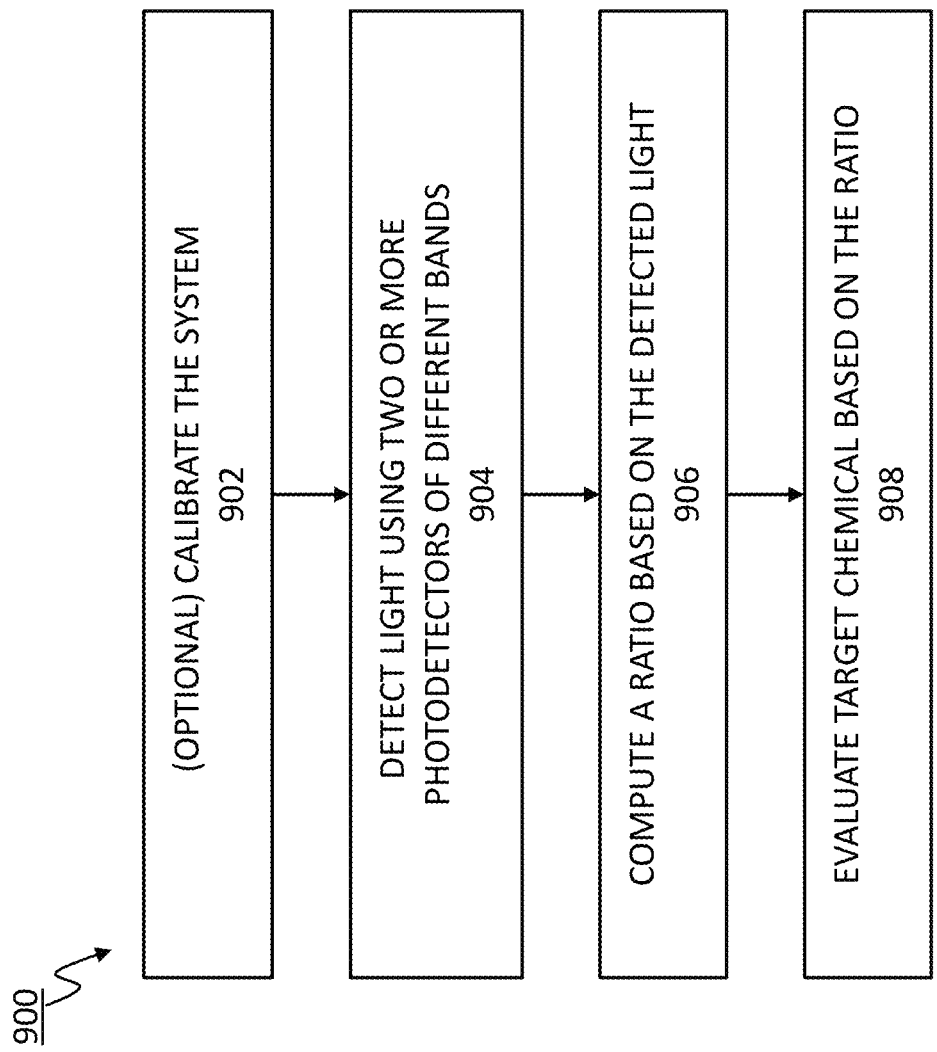
FIG. 9 illustrates a flow diagram of an optical detection method, according to some embodiments of the disclosure.

FIG. 9 illustrates a flow diagram of an optical detection method 900, according to some embodiments of the disclosure. Although described with reference to the system illustrated in FIG. 3, any systems configured to perform steps of method 900, in any order, are within the scope of the present disclosure.

At the beginning of the method, the system 300 may be calibrated (optional step 902). This may take place once, e.g. when the system 300 is being built or before the system 300 is put into operation, or may take place multiple times. During calibration, a plurality of ratios for a plurality of samples having a known presence and/or a known amount of one or more of predefined target chemicals or artificial optical filters that mimic the target chemical(s) may be computed, as described above.

Each ratio could be a ratio between at least one parameter indicative of at least the intensity, e.g. normalized intensity, of light that has interacted with the predefined target chemical as measured by one photodetector and another parameter indicative of at least the intensity, e.g. normalized intensity, of light as measured by another photodetector 302. Calibration could also include storing the plurality of computed ratios in association with identifications of the plurality of samples (i.e. identifying, for each computed ratio, the particular predefined target chemical for which the ratio was computed, as well as the known presence and/or the known amount of the predefined target chemicals in/on a sample for which the ratio was computed).

In operation, two or more photodetectors 302 would be used to detect light that has interacted with the target chemical (step 904). Results of photodetector measurements would be provided to the processing logic 304, which would then compute one or more ratios based on the intensities detected by the different photodetectors (step 906). Since the ratios are selected to be representative of the presence and/or the amount of the target chemical, the processing logic 304 could then evaluate the presence and/or the amount of the target chemical based on the computed ratio (step 908).

Specular Reflection

As the foregoing description illustrates, evaluation of the presence and/or the amount of the target chemical based on the ratios described herein requires measurements at multiple wavelengths. The measurement of the spectra, whether at two colors or more, requires great care, especially when skin is involved. In particular, in some deployments of the reflection measurement embodiments described above, specular reflection of the light generated by the light source (e.g. by the LED 310) from the object being evaluated (e.g. the object 420) could present challenges in obtaining accurate evaluation regarding the target chemicals present in the object.

Figure 10:
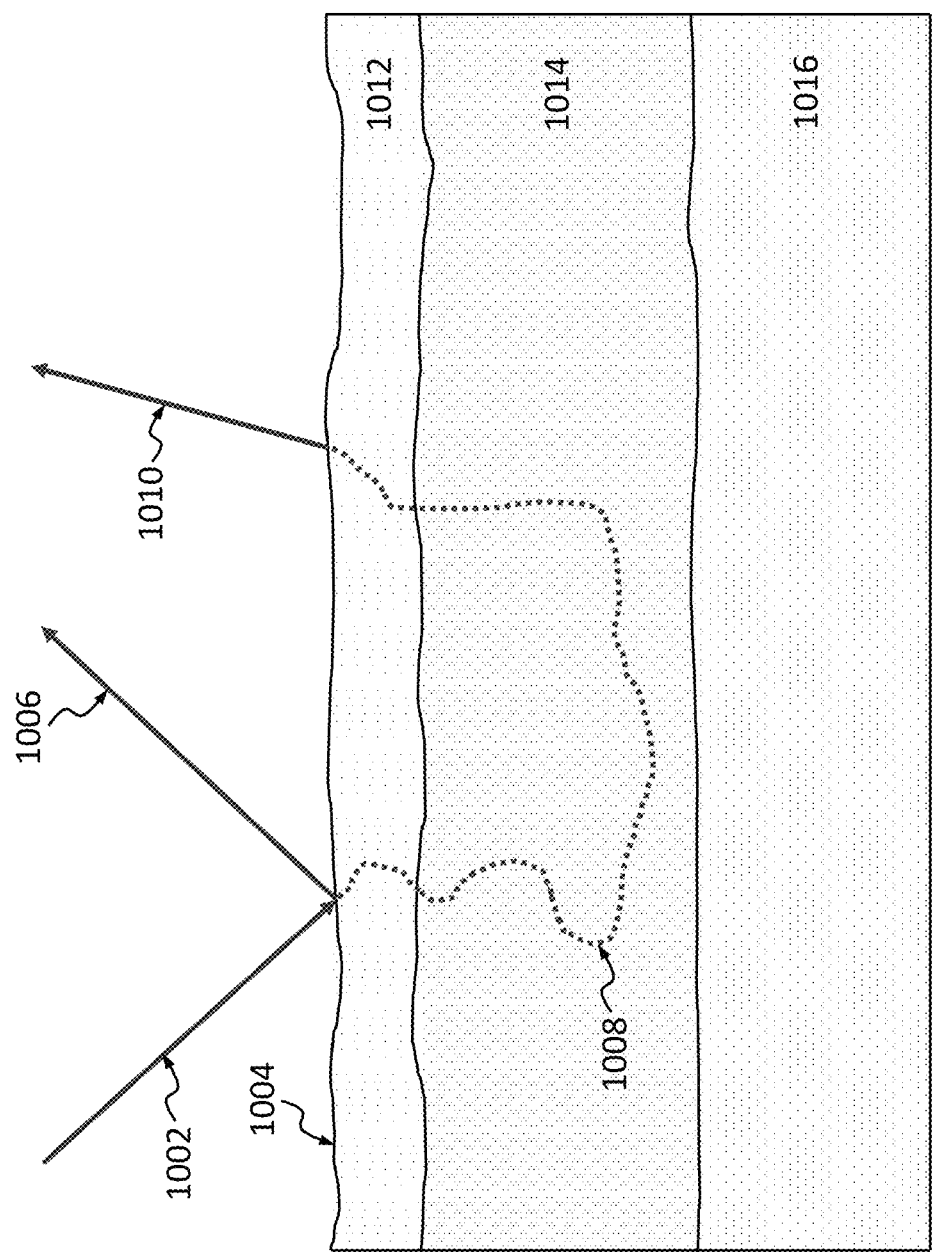
FIG. 10 illustrates specular reflection of light generated by the light source being incident on the photodetectors during reflection measurement.

This is because, as the photons impinge on the skin, some are reflected at the surface and some enter the skin, scatter inside the skin layers and a few will emerge at some distance from the incidence location. This is shown on FIG. 10 showing that, when light rays 1002 are impingent on the surface of the skin 1004, some are directly reflected, resulting in specular reflection 1006, while others enter the skin, scatter inside the skin layers, as shown in FIG. 10 with a dotted line 1008, and may emerge as light rays 1010 at some distance from the incidence location. Reference numerals 1012, 1014, and 1016 shown in FIG. 10 indicate various layers of skin.

Thus, the light rays incident on the photodetectors during reflection measurements as shown e.g. in FIG. 4A, may include both the specular rays and the non-specular rays. In fact, especially in a compact geometry where the light source and the receiving photodetector(s) are very close to one other, as shown in FIG. 4A, it can be very challenging to avoid specular component at the photodetector(s).

The specular rays carry relatively little information about the absorption and the scattering characteristics of the skin. These specularly reflected photons, for most part, represent the characteristics of the light source rather than those of the skin. For example, blood vessels are in the dermis layer of the skin which is typically at least 100 micrometers below the skin surface, and melanosomes are in the epidermis and are around 40-200 micrometers below the surface.

Figure 11:
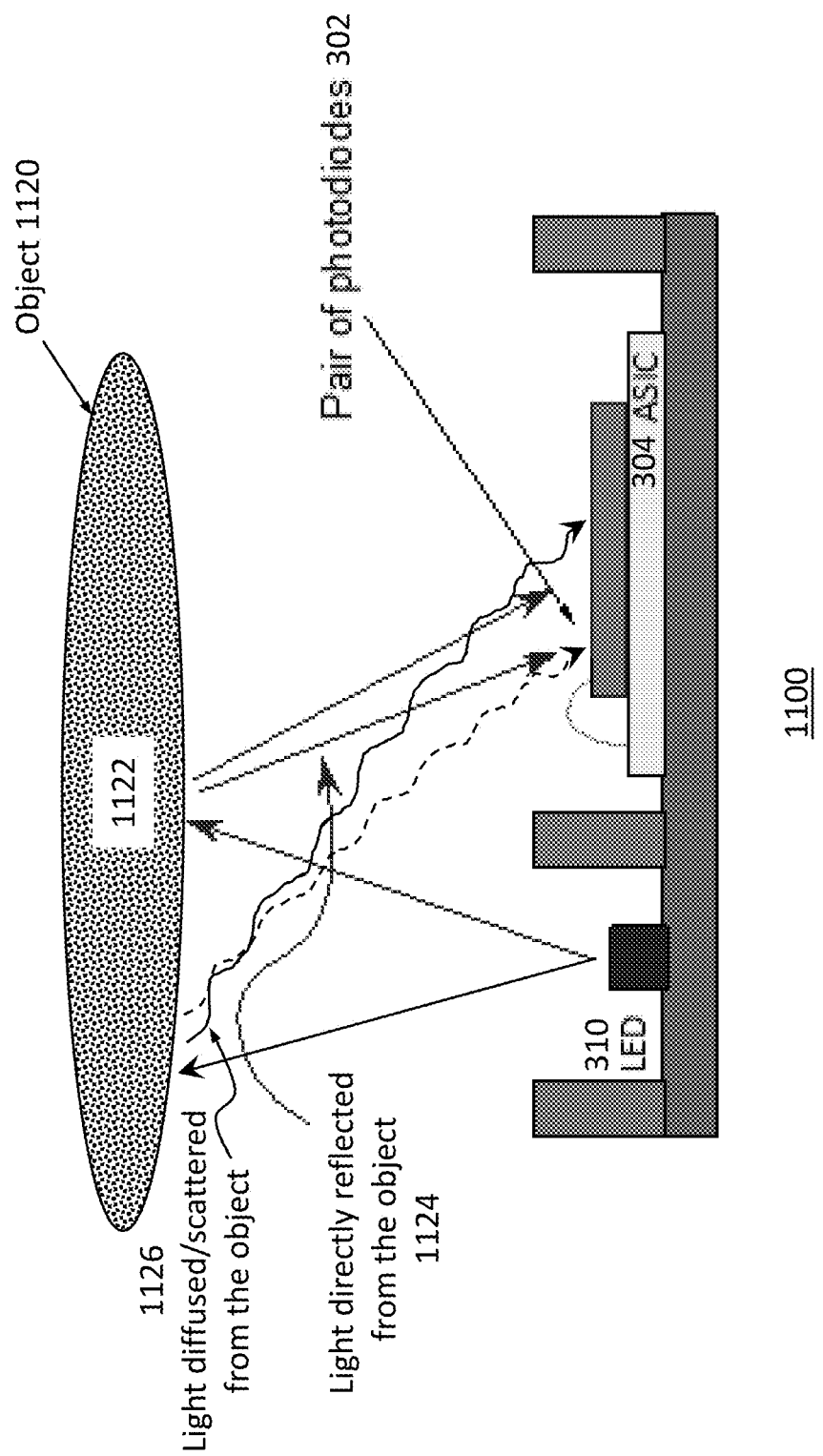
FIG. 11 illustrates relative positions of a sample and parts of an apparatus for optical detection of a presence and/or an amount of a target chemical in/on the sample for a reflection measurement configured to decrease or prevent specular reflection of light generated by the light source being incident on the photodetectors, according to some embodiments of the disclosure.

Thus, different components of the skin tissue are at different depths and their characteristic absorption and scattering properties are probed by photons that have traversed those layers. The Kubelka-Munk theory as described above and many other radiative transport models that model skin for clinical and cosmetic applications all focus on the non-specular component of the reflection as this carries most of the relevant information. FIG. 11 shows specular reflection of light generated by the light source 310 being incident on the photodetectors 302 during reflection measurements.

In FIG. 11, elements indicated by reference numerals shown in FIG. 3 are intended to represent the elements analogous to those illustrated and described with reference to FIG. 3, which description is, therefore, not repeated here. FIG. 11 is similar to FIG. 4A in that it illustrates that light generated by the light source 310 is reflected off of a sample 1120, thereby interacting with melanosomes, water, or other target chemical of interest 1122 that may be present in the sample (melanosomes, water, or any other target chemical of interest, shown as dots in the sample object 1120), and the reflected light is incident on the photodetectors 302.

FIG. 11 specifically illustrates that, during reflection measurements, two types of light generated by the LED 310 may be incident on the photodetectors 302.

One type—is light generated by the LED 310 and directly reflected from the object 1120, shown in FIG. 11 as a light contribution 1124. The light contribution 1124 may be largely attributed to specular reflection, i.e. light generated by the LED 310 and reflected from the object 1120 in a predictable manner in accordance with the law of reflection of ray optics stating that the angle of reflection is equal to the angle of incidence, the angles being measured between the reflective surface and a normal to such surface.

Another type—is light generated by the LED 310 and diffused/scattered by the object 1120, shown in FIG. 11 as a light contribution 1126. Lines 1126 shown in FIG. 11 illustrate only two lines—one line is solid and one line is dashed just to illustrated that the diffusively reflected/scattered light could propagate at different angles; in reality there will typically be many such lines. Moreover, the waviness of lines 1126 is only intended to differentiate from the straight lines of specular reflection, such as the line 1124.

Specular reflection contributions 1124 incident on the photodetectors 302 could be problematic because the photodetector 302 cannot differentiate these photons from diffused/scattered photons but, as described above, specular reflected photons do not provide information on the concentration of melanosome, water, or other target chemical in the sample object but only provide information on the light source, in this example the LED 310.

The problem of specular reflection from the skin is further exacerbated by the fact that a cover glass is often inserted between the skin and the measurement apparatus of FIG. 4A or FIG. 11 to protect the measurement module from the environment. The surfaces of this cover glass may also contribute to the specular reflection, further making the task of interpretation of the spectral components quite difficult and unreliable.

Figure 12:
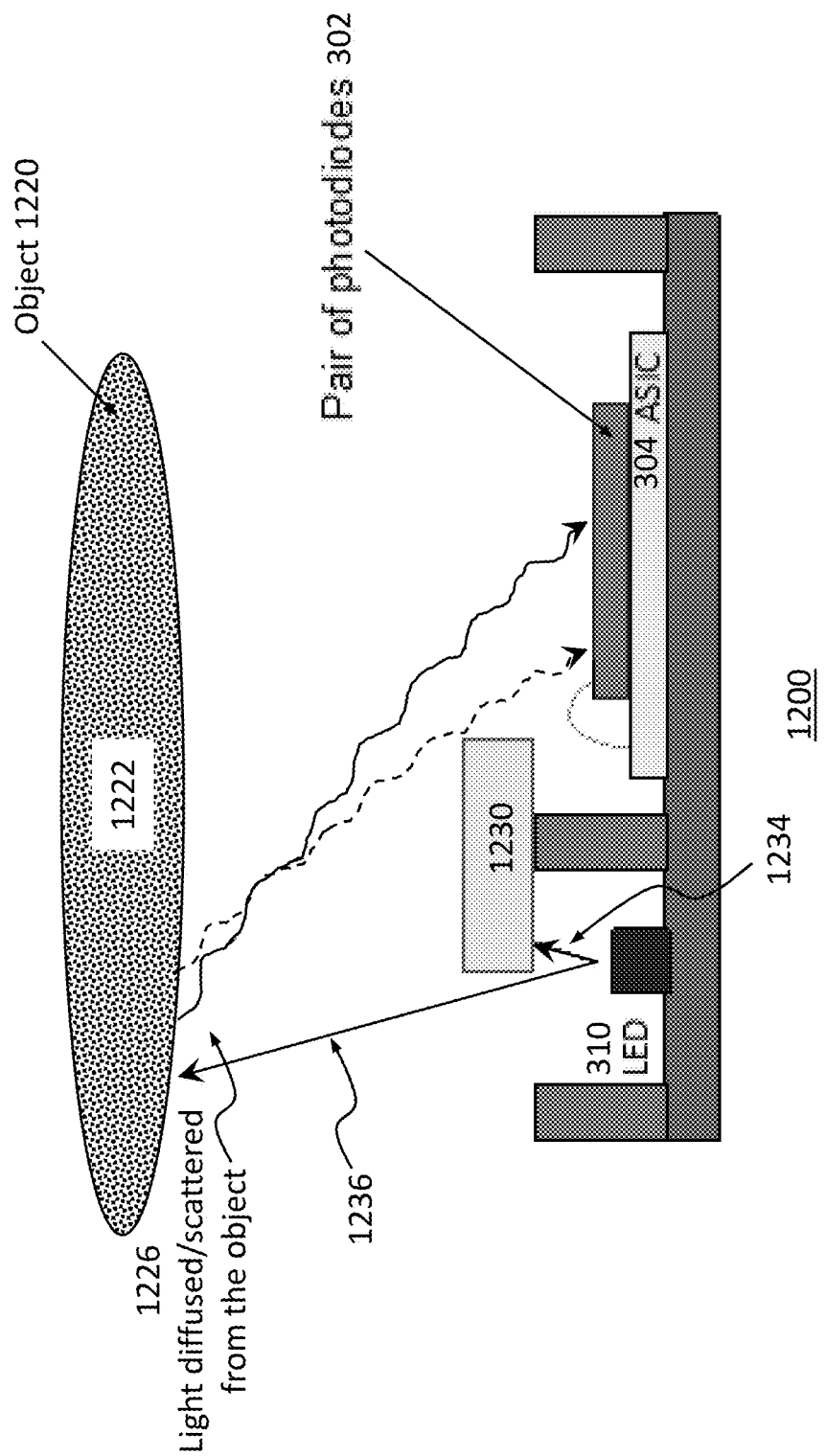
FIG. 12 illustrates an example embodiments of a non-contact apparatus for optical detection of target chemicals in accordance with embodiments of the present disclosure.

In order to overcome or at least minimize these problems, in some embodiments of the present disclosure where reflective measurements are employed, a structure is described that would be configured to block at least some of the light generated by the LED 310 that may be likely to result in specular reflection on the photodetectors 302. FIG. 12 illustrates one example of such a structure as a structure 1230. FIG. 12 provides an illustration similar to that shown in FIG. 11 and therefore, unless specified otherwise, discussions of elements with the same or similar reference numerals provided for FIG. 11 are applicable to corresponding elements of FIG. 12 and, therefore, in the interests of brevity, not repeated here.

The structure 1230 shown in FIG. 12 comprises a T-like structure comprising a substantially vertical portion at a substantially horizontal portion and provided in such a manner that at least a portion of light generated by the LED 310 and incident on the object 1220 that is likely to result in specular reflection, that portion shown in FIG. 12 as LED light contribution 1234, is blocked by the structure 1230.

The portion of light generated by the LED 310 could be likely to result in specular reflection from the object 1220 which would be incident on the photodetectors 302 could be determined, using the law of reflection, based on the relative locations of the LED 310 and the photodetectors 302 (known at the time of fabrication the device) and possible locations of the object 1220 (which could be estimated for typical use-case scenarios). The shape and the position of a structure to block at least part or all of directly reflected light could then be determined.

The example illustrated in FIG. 12 shows that, in some embodiments, the structure 1230 could be provided between the LED 310 and the photodetectors 302 and extend as to block LED light rays which are propagating in the direction of the photodetectors 302 (e.g. the LED light contribution 1234). This is a simple illustration because, in accordance with the law of reflection, specular reflected light of the light rays generated by the LED 310 which propagate in directions away from the photodetectors 302 (e.g. the LED light contribution 1236) would not be incident on the photodetectors 302.

The LED light contributions 1236 may still be specularly reflected from the object 1220, but because such reflected light will not be incident on the photodetectors 302, or at least presence of such reflected light incident on the photodetectors 302 would be reduced or minimized, it would not present problems or at least reduce problems with the measurements carried out by the system. In other words, because the structure 1230 is configured to block those rays from the LED 310 which are specularly reflected towards the photodetector 302, the rays that do reach the photodetector 302 are, by design, those that have traversed inside the skin and provide useful information about the skin (or, at the very least, the structure 1230 increases the amount of such rays compared to specularly reflected rays incident on the photodetector).

Structure shown as the structure 1230 of FIG. 1230 provides only one example of a possible structure that could be configured to prevent, minimize, or at least decrease specular reflection of the light generated by the LED 310 being incident on the photodetectors 302. Based on the descriptions provided above, a person of ordinary skill in the art can envision a large variety of such structures, all of which are within the scope of the present disclosure.

Furthermore, such structures configured to prevent, minimize, or at least decrease specular reflection of light generated by a light source of a module being incident on a photodetector of the same module may be applied to any combination of light sources and photodetectors. For example, for hydration, a single broadband LED and filtered detectors to measure water content may be used; for Erythema or melanin, a white light LED and multiple suitably filtered photodiodes to measure light at specific colors may be used. Alternately, multiple colored light sources, e.g. LEDs (red, green, blue, IR etc.) can be used and the reflection be measured by blinking LEDs in quick succession.

Still further, structures configured to prevent, minimize, or at least decrease specular reflection of light generated by a light source of a module being incident on a photodetector of the same module, as described herein, may be used in other modules performing optical measurements, such as e.g. in pulse oximetry.

Specular reflection blocking structures as described herein may also be used in activity monitors and smart watches utilizing optical measurements using a technique called photoplethysmography (PPG). Such activity monitors and smart watches are becoming widely popular, and users expect to get an increasingly accurate estimate of their heart rate (HR) from these devices rather than wear uncomfortable but more accurate chest straps.

Similar to the measurement modules described above in context of evaluation of skin type and condition, these HR measuring devices are equipped with a light source, e.g. an LED, and a photodetector which enable estimation of HR by optical measurements using the PPG technique. The LED illuminates the back of the wrist and the backscattered light is recorded by the optical sensor. The HR can then be estimated by measuring the period of the fluctuations of the optical signal, caused by the periodic change in the amount of blood in the wrist and the resulting change in light absorption with each beat of the heart. Such HR measurement systems would also benefit from reducing the amount of specular reflection from the LED of the module being incident on the photodetector of the module.

The signal of interest for material characterization by practical necessity includes ratios to remove common variations that do not go towards clear identification of property of interest. So, in FIG. 2, we can ratio the light coming at two different wavelengths or form multiple ratios for three wavelengths to identify the characteristics of the skin. The ratio could also take the form of scattered light measured at different locations by two different photodetectors. These ratios or ratios of ratios or similar analysis can be carried out to improve material measurement.

In summary, embodiments described herein allow providing a relatively low cost alternative to a full spectrometer for monitoring target chemicals, e.g. melanosomes, and thus determining whether a sample being examined is a skin sample and/or determining skin type and condition. Systems proposed herein are simpler than a spectrometer because they are compact, and are directly able to measure the target chemical and use fewer, at least two, wavelengths for the analysis. Employing two photodetectors with appropriate calibration procedure and computation of ratios or ratio of ratios provides independence from gain as well as allows smoothly changing background reflectance as described herein.

Resulting modules may be made compact and low power. By modulating the light emitted by the light source(s), effects of ambient light may be eliminated. Furthermore, systems proposed herein are easy to calibrate against a standard and adapted to the target chemical and the test object (i.e. the object/sample in/on which the target chemical is provided), and more than one chemical measurement may be carried out by using more than one light source and/or multiple photodetectors.

In addition, embodiments disclosed herein provide structures which could prevent, minimize, or at least decrease the amount of specular reflected light being incident on photodetectors during optical reflection measurements, which could result in more accurate readings. Such structures could be used in combination with the embodiments of skin type and condition evaluation, in evaluation of content of an target chemical in objects other than skin, as well as in any optical measurement systems where a light source and a photodetector configured to analyze light generated by the light source as scattered/diffused by an object are employed, e.g. in HR measurement systems employing PPG.

Structures configured to prevent, minimize, or at least decrease specular reflection of light as described herein may be particularly useful in small form factor modules, e.g. where the light source and the photodetectors are separated by a distance less than 5 millimeters (mm), including all values and ranges therein, e.g. by a distance between 1.5 and 4 mm, or/and where the largest dimension of the entire module is less than 7-8 mm. In such small form factor modules, a light source and one or more photodetectors could be provided on the same die or on the same printed circuit board (PCB).

Figure 13:
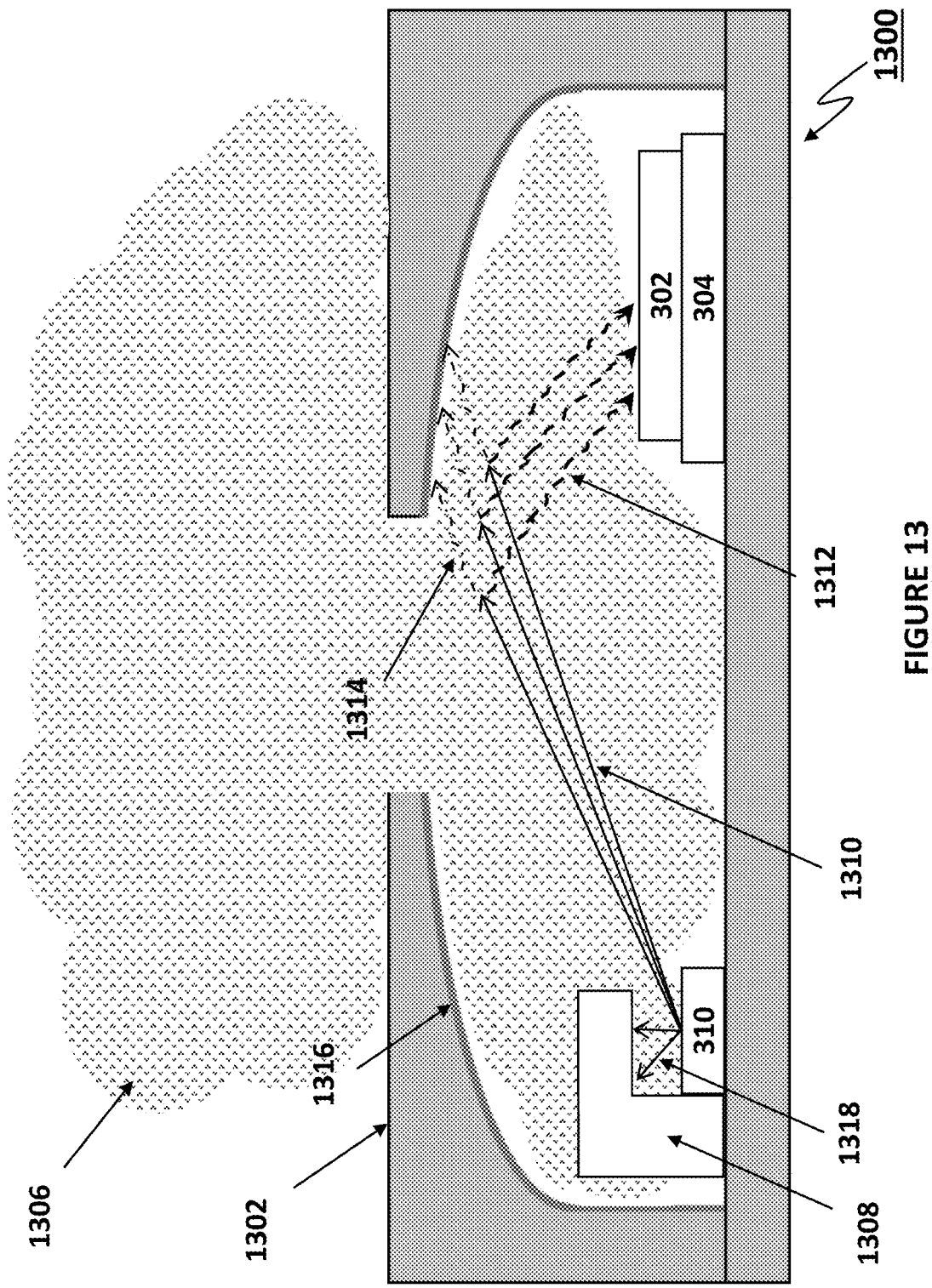
FIG. 13 illustrates an example embodiments optical detection of target chemicals which blocks specular reflections, in accordance with embodiments of the present disclosure.

FIG. 13 is a schematic diagram of a smoke detector 1300 in accordance with embodiments of the present disclosure. The smoke detector 1300 can include a housing 1302 that houses a light emitting device 310. The light emitting device 310 can emit light of wavelengths depending on the application. For example, the light emitting device can emit blue light or infrared light (e.g., 1400 nm light), or a combination of light sources. The light emitted 1310 can interact with smoke 1306 or other pollutants. The light back scattered 1312 from the smoke 1306 can be detected by a photodetector 302 and processed by ASIC 304. Light 1314 that passes through the smoke can be absorbed by the housing 1302.

In embodiments, the housing 1302 can include a structure 1308. Structure 1308 can be designed to block specular reflection from the emitting light that is reflected from the inner surface of housing 1302. The inner housing 1302 can be lined with a black material or other light absorption material 1316 to assist in reducing the detection of specular reflections, but the absorption material 1316 can become dirty over time, compromising the absorption properties. The structure 1308 can block some of the emitted light from the light emitting device 310.

The structure 1308 shown in FIG. 13 includes an L-shaped structure comprising a substantially vertical portion at a substantially horizontal portion and provided in such a manner that at least a portion of light generated by the light emitting device 310 and incident on the smoke 1306 that is likely to result in specular reflection, that portion shown in FIG. 13 as LED light contribution 1318, is blocked by the structure 1308.

The portion of light generated by the light emitting device 310 could be likely to result in specular reflection from the smoke 1308 which would be incident on the photodetectors 302 could be determined, using the law of reflection, based on the relative locations of the light emitting device 310 and the photodetectors 302 (known at the time of fabrication the device) and possible locations of the smoke 1308 (which could be estimated for typical use-case scenarios). The shape and the position of a structure to block at least part or all of directly reflected light could then be determined.

The example illustrated in FIG. 13 shows that, in some embodiments, the structure 1308 could be provided on an opposite side of the light emitting device 310 and the photodetectors 302 and extend as to block LED light rays which are propagating in the direction that is different than the direction of the photodetectors 302 (e.g. the LED light contribution 1318). This is a simple illustration because, in accordance with the law of reflection, specular reflected light of the light rays generated by the LED 310 which propagate in directions away from the photodetectors 302 (e.g., the LED light contribution 1310) would not be incident on the photodetectors 302, with the exception of the light reflected from the inner wall of the housing 1302 (e.g., as the absorption material 1316 on the inner wall of the housing 1302 gets dirty).

The LED light contributions 1310 may still be specularly reflected from the smoke 1308, but because such reflected light will not be incident on the photodetectors 302, or at least presence of such reflected light incident on the photodetectors 302 would be reduced or minimized, it would not present problems or at least reduce problems with the measurements carried out by the system. In other words, because the structure 1308 is configured to block those rays from the light emitting device 310 which are specularly reflected towards the photodetectors 302, the rays that do reach the photodetector 302 are, by design, those that have traversed inside the skin and provide useful information about the skin (or, at the very least, the structure 1308 increases the amount of such rays compared to specularly reflected rays incident on the photodetector).

Structure shown as the structure 1308 of FIG. 13 provides only one example of a possible structure that could be configured to prevent, minimize, or at least decrease specular reflection of the light generated by the light emitting device 310 being incident on the photodetectors 302. Based on the descriptions provided above, a person of ordinary skill in the art can envision a large variety of such structures, all of which are within the scope of the present disclosure.

While the present disclosure primarily focuses on chemical detection, other devices are not beyond the scope of the invention. For example, gaseous chemical identification and detection are entirely applicable.

Select Examples

Example A1 provides an apparatus for optical detection of a presence and/or an amount of a target chemical, e.g. melanosomes. The apparatus includes a first photodetector configured to detect light of a first wavelength that has interacted with the target chemical, and a second photodetector configured to detect light of a second wavelength that has interacted with the target chemical, the second wavelength being different from the first wavelength.

The apparatus further includes a processing logic configured to compute a ratio (R) between a first parameter indicative of at least an intensity of the light detected by the first photodetector (Int1) (possibly indicative of a combination of intensities of the light detected by each of the first and second photodetectors) and a second parameter indicative of at least an intensity of the light detected by the second photodetector (Int2), and determine the presence and/or the amount of the target chemical based on the computed ratio.

Example A2 provides the apparatus according to Example A1, where the first photodetector is configured to detect light of a first band of wavelengths that has interacted with the target chemical, the first band of wavelengths including the first wavelength, and the second photodetector is configured to detect light of a second band of wavelengths that has interacted with the target chemical, the second band of wavelengths including the second wavelength.

Example A3 provides the apparatus according to Example A2, where the first band of wavelengths and the second band of wavelengths at least partially overlap.

Example A4 provides the apparatus according to Example A3, where the first band of wavelengths is included within the second band of wavelengths and the ratio is computed as $$R = \frac{\alpha Int1 - \beta(Int2 - Int1)}{Int2},$$

where $\alpha$ and $\beta$ are predefined parameters.

Example A5 provides the apparatus according to Example A2, where the first band of wavelengths and the second band of wavelengths do not overlap and the ratio is computed as $$R = \frac{Int2 - Int1}{Int2 + Int1}, R = \frac{Int2}{Int1},$$
$$R = \frac{Int2 + Int1}{Int2 - Int1}, \text{ or } R = \frac{Int1}{Int2}.$$

Example A6 provides the apparatus according to any one of the preceding Examples, where the first photodetector is provided at a distance less than 5 millimeters from the second photodetector.

Example A7 provides the apparatus according to any one of Examples A1-5, where each of the first photodetector and the second photodetector includes a plurality of photodetection regions, and the photodetection regions of the first photodetector are interleaved with the photodetection regions of the second photodetector.

Example A8 provides the apparatus according to Examples A6 or 7, where the first photodetector and the second photodetector are provided on the same die.

Example A9 provides the apparatus according to any one of the preceding Examples, where the first photodetector is configured to detect the light of the first wavelength by detecting light incident on one or more photodetection regions of the first photodetector that has passed through a first optical filter and the second photodetector is configured to detect the light of the second wavelength by detecting light incident on one or more photodetection regions of the second photodetector that has passed through a second optical filter.

Example A10 provides the apparatus according to Example A9, where the first optical filter and/or the second optical filter is provided as a coating over a respective photodetector.

Example A11 provides the apparatus according to any one of the preceding Examples, where the light of the first wavelength is modulated and the light detected by the first photodetector is locked to the modulation of the light of the first wavelength, and/or the light of the second wavelength is modulated and the light detected by the second photodetector is locked to the modulation of the light of the second wavelength. In this manner, contamination from the ambient light at the first and/or second wavelengths may be reduced or eliminated.

Example A12 provides the apparatus according to any one of the preceding Examples, where the first photodetector is configured to detect light of the first wavelength substantially simultaneously with, or at least temporally overlapping, the second photodetector detecting light of the second wavelength. In this manner, potential motion induced artifacts, such as e.g. when measuring skin hydration on the hands and the hands not being held steady or when measuring moisture in industrial process control and samples being evaluated moving on a conveyer belt, may be reduced or eliminated.

Example A13 provides the apparatus according to any one of the preceding Examples, further including one or more light sources configured to generate light to interact with the target chemical, the light including at least the light of the first wavelength (or of the first band of wavelengths including the first wavelength) and the light of the second wavelength (or of the second band of wavelengths including the second wavelength).

Example A14 provides the apparatus according to Example A13, where the light generated by the one or more light sources includes broadband light (e.g. extended white light including wavelengths in the range of 1300-1600 nm or in the range of 1800-2000 nm for water measurements, in the range of 1600-1800 nm or in the range of 1100-1300 for fat or oil measurements, etc.).

Example A15 provides the apparatus according to Example A14, where a band of the light generated by the one or more light sources at least partially overlaps with a band of light that the first photodetector is configured to detect and with a band of light that the second photodetector is configured to detect.

Example A16 provides the apparatus according to any one of Examples A13-15, where the one or more light sources include a light emitting diode centered at about 1460 nm or/and a light emitting diode centered at about 1930 nm, and the target chemical includes, or is, water.

Example A17 provides the apparatus according to any one of Examples A13-15, where the one or more light sources include a light emitting diode centered at about 1200 nm, and the target chemical includes, or is, a fat.

Example A18 provides the apparatus according to any one of the preceding Examples, further including a third photodetector configured to detect light of a third wavelength that has interacted with the target chemical, the third wavelength being different from the first and the second wavelengths, where the processing logic determining the ratio includes the processing logic determining one or more ratios between the first parameter, the second parameter, and a third parameter indicative of at least an intensity of the light detected by the third photodetector (Int3), and the processing logic determining the presence and/or the amount of the target chemical based on the computed ratio includes the processing logic determining the presence and/or the amount of the target chemical based on the determined one or more ratios.

Example A19 provides a method for optical detection of a presence and/or an amount of a target chemical. The method includes computing a ratio (R) between a first parameter indicative of at least an intensity of light of a first wavelength that has interacted with the target chemical, detected by a first photodetector (Int1) (possibly indicative of a combination of intensities of the light detected by each of the first and second photodetectors) and a second parameter indicative of at least an intensity of the light of a second wavelength that has interacted with the target chemical, the second wavelength being different from the first wavelength, detected by a second photodetector (Int2); and determining the presence and/or the amount of the target chemical based on the computed ratio.

Example A20 provides the method according to Example A19, further including performing a calibration, prior to determining the presence and/or the amount of the target chemical, by computing a plurality of ratios for a plurality of samples having a known presence and/or a known amount of one or more of predefined target chemicals, each ratio including a ratio between the first parameter indicative of at least the intensity of light of the first wavelength that has interacted with the predefined target chemical and the second parameter indicative of at least the intensity of light of the second wavelength that has interacted with the predefined target chemical; and storing the plurality of computed ratios in association with identifications of the plurality of samples (i.e. identifying, for each computed ratio, the particular predefined target chemical for which the ratio was computed, as well as the known presence and/or the known amount of the predefined target chemicals in/on a sample for which the ratio was computed).

Variations and Implementations

It is noted that the illustrations in the FIGURES do not necessary represent true layout, orientation, sizing, and/or geometry of an actual apparatus/assembly for optical detection of a presence and/or an amount of a target chemical as well as an actual apparatus/assembly for optical measurement of light scattered/diffused by an object. It is envisioned by the disclosure that various suitable layouts can be designed and implemented for apparatus/assembly configured to detect a presence and/or an amount of a target chemical based on a computed ratio of parameters indicative of intensities of light measured by different photodetectors. Similarly, various suitable layouts can be designed and implemented for apparatus/assembly configured to prevent, minimize, or at least decrease the amount of specularly reflected light in optical measurements of light scattered/diffused by an object.

Based on the descriptions provided above, a person of ordinary skill in the art can easily envision various further embodiments and configurations for determining present/content of a target chemical using photodetectors configured to detect light in different bands, all of which are within the scope of the present disclosure. To that end, FIGS. 2-9 and 12 can vary significantly to achieve equivalent or similar results, and thus should not be construed as the only possible implementation which leverages the use of ratios disclosed herein.

Similarly, based on the descriptions provided above, a person of ordinary skill in the art can easily envision various further embodiments and configurations for providing structures configured to prevent, minimize, or at least decrease the amount of specularly reflected light in optical measurements of light scattered/diffused by an object (such structures referred to herein sometime simply as "blocking structures").

It is envisioned that the apparatus/assembly described herein and/or the associated processing modules can be provided in many areas including medical equipment, security monitoring, patient monitoring, healthcare equipment, medical equipment, automotive equipment, aerospace equipment, consumer electronics, and sports equipment, etc.

In some cases, the apparatus/assembly and/or the associated processing module can be used in professional medical equipment in a healthcare setting such as doctor's offices, emergency rooms, hospitals, etc. In some cases, the apparatus/assembly and/or the associated processing module can be used in less formal settings, such as schools, gyms, homes, offices, outdoors, under water, etc. The apparatus/assembly and/or the associated processing module can be provided in a consumer healthcare product.

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure. For instance, instead of processing the signals in the digital domain, it is possible to provide equivalent electronics that can process the signals in the analog domain.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself.

In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities. In some cases, application specific hardware can be provided with or in the processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the target chemical detection functionalities described herein may be implemented in one or more silicon cores in Application Specific Integrated Circuits (ASICs), Field Programmable Gate Arrays (FPGAs), and other semiconductor chips.

Note that the activities discussed above with reference to the FIGURES are applicable to any integrated circuits that involve signal processing, particularly those that can execute specialized software programs, or algorithms, some of which may be associated with processing digitized real-time data to detect chemical content. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems. Moreover, certain embodiments discussed above can be provisioned in digital signal processing technologies for medical imaging, patient monitoring, medical instrumentation, and home healthcare. This could include pulmonary monitors, heart rate monitors, pacemakers, etc. Other applications can involve automotive technologies for safety systems (e.g., stability control systems, driver assistance systems, braking systems, infotainment and interior applications of any kind). In yet other example scenarios, the teachings of the present disclosure can be applicable in the industrial markets that include process control systems aiming to track vital signs to help drive productivity, energy efficiency, and reliability.

Note that with the numerous examples provided herein, interaction may be described in terms of two, three, four, or more parts. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of the present disclosure. In certain cases, it may be easier to describe one or more of the functionalities of a given set of flows by only referencing a limited number of electrical elements. It should be appreciated that the features of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in the present disclosure, references to various features (e.g., elements, structures, modules, components, steps, operations, parts, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to measuring chemical content and functions related to other optical measurements, e.g. using PPG, illustrate only some of the possible functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An optical detector detecting a predetermined chemical which mitigates specular reflection comprising:
    a light source configured to emit light comprising a first and second wavelength;
    a first optical filter configured to pass light at an optical bandwidth centered about the first wavelength;
    a first photodetector disposed proximally to the first optical filter configured to detect light in the optical bandwidth centered about the first wavelength that has interacted with the target chemical;
    a second optical filter configured to pass light at an optical bandwidth centered about the second wavelength;
    a second photodetector disposed proximally to the second optical filter configured to detect light in the optical bandwidth centered about the second wavelength;
    a circuit configured to receive a first current from the first photodetector and a second current from the second photodetector; and
    processing logic in electrical communication with the circuit configured to:
        compute a first ratio based on the first current and the second current;
        compute a second ratio based on the first current and the second current; and
        determine at least one of the presences and the amount of the target chemical based on the computed ratio of ratios.

2. The optical detector detecting a predetermined chemical which mitigates specular reflection of claim 1 wherein the light source emits broadband light.

3. The optical detector detecting a predetermined chemical which mitigates specular reflection of claim 2 wherein the ratio is computed as one of:
    ratio=((second current)−(first current))/((second current)+(first current)),
    ratio=(second current)/(first current),
    ratio=((second current)+(first current))/((second current)−(first current)),
    ratio=(first current)/(second current).

4. The optical detector detecting a predetermined chemical which mitigates specular reflection of claim 2, wherein the light source is a broadband LED.

5. The optical detector detecting a predetermined chemical which mitigates specular reflection of claim 1, wherein the optical bandwidth centered about the first wavelength and the optical bandwidth centered about the second wavelength at least partially overlap.

6. The optical detector detecting a predetermined chemical which mitigates specular reflection of claim 5, wherein a first band of wavelengths is included within a second band of wavelengths and is computed as:
    ratio=($\alpha$(first current)−$\beta$((second current)−(first current))/(second current), where $\alpha$ and $\beta$ are predefined parameters.

7. The optical detector detecting a predetermined chemical which mitigates specular reflection of claim 1, wherein the first photodetector is provided at a distance less than 5 millimeters from the second photodetector.

8. The optical detector detecting a predetermined chemical which mitigates specular reflection of claim 1, wherein each of the first photodetector and the second photodetector comprises a plurality of photodetection regions, and the photodetection regions of the first photodetector are interleaved with the photodetection regions of the second photodetector.

9. The optical detector detecting a predetermined chemical which mitigates specular reflection of claim 8, wherein the first photodetector and the second photodetector are provided on a same die.

10. The optical detector detecting a predetermined chemical which mitigates specular reflection of claim 1, wherein at least one of the first optical filter and the second optical filter is provided as a coating over a respective photodetector.

11. The optical detector detecting a predetermined chemical which mitigates specular reflection of claim 1, wherein the light of the first wavelength is modulated and the light detected by the first photodetector is locked to the modulation of the light of the first wavelength, and/or the light of the second wavelength is modulated and the light detected by the second photodetector is locked to the modulation of the light of the second wavelength.

12. The optical detector detecting a predetermined chemical which mitigates specular reflection of claim 1, wherein the first photodetector is configured to detect light centered about the first wavelength simultaneously with the second photodetector detecting light centered about the second wavelength.

13. The optical detector detecting a predetermined chemical which mitigates specular reflection of claim 1, wherein the light source comprises a light emitting diode centered substantially about 1460 nm and a light emitting diode centered about 1930 nm, and the target chemical comprises water.

14. The optical detector detecting a predetermined chemical which mitigates specular reflection of claim 1, wherein the light source comprises a light emitting diode centered at 1200 nm, and the target chemical comprises a fat.

15. The optical detector detecting a predetermined chemical which mitigates specular reflection of claim 1, further comprising a third photodetector configured to detect light of a third wavelength that has interacted with the target chemical, wherein:
the processing logic determining the ratio comprises the processing logic determining one or more ratios between the first current, the second current, and a third current from the third photodetector, and the processing logic determining the amount of the target chemical based on the computed ratio comprises the processing logic determining the amount of the target chemical based on the determined one or more ratios.

16. A method for optical detection of a presence and an amount of a target chemical, the method comprising:
emitting light comprising a first and second wavelength from a light source;
filtering light outside an optical bandwidth centered about the first wavelength to obtain a first filtered light;
detecting the first filtered light using a first photodetector configured to detect light that has interacted with the target chemical;
filtering light outside an optical bandwidth centered about the second wavelength to obtain a second filtered light;
detecting the second filtered light using a second photodetector;
electrically communicating a first signal from the first photodetector, and a second signal from the second photodetector;
computing a first ratio based on the first current and the second current;
computing a second ratio between the first signal and the second signal; and
determining at least one of the presences and the amount of the target chemical based on a computed ratio or ratios.

17. The method according to claim 16, further comprising performing a calibration, prior to determining the presence and/or the amount of the target chemical, by:
computing a plurality of ratios for a plurality of samples having a known presence and/or a known amount of one or more of predefined target chemicals, each ratio comprising a ratio between the first signal indicative of at least the intensity of light of the first wavelength that has interacted with the predefined target chemical and the second signal indicative of at least the intensity of light of the second wavelength that has interacted with the predefined target chemical; and
storing the plurality of computed ratios in association with identifications of the plurality of samples.

18. An apparatus for optical detection of a presence and amount of a target chemical, the apparatus comprising:
means for emitting light comprising a first and second wavelength;
means for filtering light outside an optical bandwidth centered about the first wavelength to obtain a first filtered light;
means for detecting the first filtered light using a first photodetector configured to detect light that has interacted with the target chemical;
means for filtering light outside an optical bandwidth centered about the second wavelength to obtain a second filtered light;
means for detecting the second filtered light using a second photodetector;
means for electrically communicating a first signal from the first photodetector, and a second signal from the second photodetector;
means for computing a second ratio between the first signal and the second signal;
wherein, the means for computing is also configured to determine at least one of the presences and the amount of the target chemical based on the computed ratio of ratios.

19. The apparatus according to claim 18, wherein the means for emitting light comprises a broadband LED.

20. The apparatus according to claim 19, wherein the optical bandwidth centered about the first wavelength and the optical bandwidth centered about the second wavelength at least partially overlap.

* * * * *